United States Patent
Dai et al.

(10) Patent No.: US 10,392,272 B2
(45) Date of Patent: Aug. 27, 2019

(54) MODULATION OF ION TRANSPORT IN A LIQUID BY APPLICATION OF AN ELECTRIC POTENTIAL ON A MESOPOROUS CARBON MEMBRANE

(71) Applicant: UT-Battelle, LLC, Oak Ridge, TN (US)

(72) Inventors: Sheng Dai, Knoxville, TN (US); Shannon Mark Mahurin, Lenoir City, TN (US); Xiqing Wang, Mason, OH (US); Sumedh Pradeep Surwade, Greenville, DE (US); Ivan Vlassiouk, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 679 days.

(21) Appl. No.: 14/633,412

(22) Filed: Feb. 27, 2015

(65) Prior Publication Data
US 2016/0250596 A1 Sep. 1, 2016

(51) Int. Cl.
*C02F 1/46* (2006.01)
*B01D 61/42* (2006.01)
(Continued)

(52) U.S. Cl.
CPC .......... *C02F 1/4604* (2013.01); *B01D 61/422* (2013.01); *B01D 69/02* (2013.01);
(Continued)

(58) Field of Classification Search
CPC .... C02F 1/4604; C02F 1/4698; C02F 1/4691; C02F 1/469; B01D 61/422; B01D 61/44;
(Continued)

(56) References Cited

U.S. PATENT DOCUMENTS

| | | | |
|---|---|---|---|
| 6,042,701 A * | 3/2000 | Lichtwardt | B01D 61/52 204/229.6 |
| 8,114,510 B2 | 2/2012 | Dai et al. | |

(Continued)

FOREIGN PATENT DOCUMENTS

WO WO 2013/170249 A1 11/2013

OTHER PUBLICATIONS

Surwade et al. Electrochemical control of ion transport through a mesoporous carbon membrane. Langmuir 30 (2014) 3606-3611.*

(Continued)

*Primary Examiner* — Katherine Zalasky
(74) *Attorney, Agent, or Firm* — Scully, Scott, Murphy & Presser, P.C.

(57) ABSTRACT

A method for regulating ion transport between first and second regions of a liquid solution containing ionic species in at least one of said first and second regions, the method comprising applying a voltage on an electrically conductive mesoporous carbon membrane situated between said first and second regions of the liquid solution, wherein liquid flow between first and second regions is permitted only through said mesoporous carbon membrane, and the applied voltage is selected to modulate the degree of ion transport between said first and second regions, wherein an increase in applied voltage results in a reduction in the degree of ion transport between said first and second regions, optionally up to a critical voltage at which ion transport ceases.

20 Claims, 7 Drawing Sheets

(1A)   (1B)

(51) Int. Cl.
*B01D 61/54* (2006.01)
*B01D 69/02* (2006.01)
*B01D 71/02* (2006.01)
*C02F 1/469* (2006.01)
*C02F 103/08* (2006.01)
*A61K 9/00* (2006.01)

(52) U.S. Cl.
CPC .......... *B01D 71/021* (2013.01); *C02F 1/4698* (2013.01); *A61K 9/0009* (2013.01); *B01D 61/54* (2013.01); *B01D 2311/20* (2013.01); *B01D 2313/36* (2013.01); *B01D 2325/02* (2013.01); *C02F 2103/08* (2013.01); *Y02W 10/37* (2015.05)

(58) Field of Classification Search
CPC ...... B01D 61/54; B01D 69/02; B01D 71/021; B01D 2311/20; B01D 2313/365; B01D 2325/02
See application file for complete search history.

(56) References Cited

U.S. PATENT DOCUMENTS

| | | | |
|---|---|---|---|
| 8,828,533 B2 | 9/2014 | Dai et al. | |
| 8,865,351 B2 | 10/2014 | Mayes et al. | |
| 2004/0217014 A1* | 11/2004 | Ovshinsky | C02F 1/4604 205/742 |
| 2006/0057051 A1 | 3/2006 | Dai et al. | |
| 2011/0198225 A1* | 8/2011 | Kim | B01D 57/02 204/452 |
| 2011/0220574 A1 | 9/2011 | Bakajin et al. | |
| 2012/0085094 A1* | 4/2012 | Davis | B01D 1/0035 60/641.8 |
| 2012/0234694 A1 | 9/2012 | Vecitis et al. | |
| 2013/0183511 A1* | 7/2013 | Dai | B82Y 30/00 428/220 |
| 2014/0227325 A1 | 8/2014 | Naskar et al. | |
| 2014/0294701 A1 | 10/2014 | Dai et al. | |

OTHER PUBLICATIONS

Guan et al. Voltage gated ion and molecule transport in engineered nanochannels: theory, fabrication and applications. Nanotechnology 25 (2014) 122001, 19 pages.*
Fan et al. Gated proton transport in aligned mesoporous silica films. Nature Materials. vol. 7 (2008) p. 303-307. (Year: 2008).*
Corry B., "Designing Carbon Nanotube Membranes for Efficient Water Desalination", J. Phys. Chem. B. 112 (5):1427-1434 (2008).
Fulvio P.F. et al., "Brick-and-Mortar-Self-Assembly Approach to Graphitic Mesoporous Carbon Nanocomposites", Advanced Functional Materials 21:2208-2215 (2011), and Supporting Material.
Hou C-H et al., "Molecular-Sieving Capabilities of Mesoporous Carbon Membranes", J. Phys. Chem. B 112 (29):8563-8570 (2008).
Hou C-H et al., "Electrosorption Capacitance of Nanostructured Carbon-Based Materials", Journal of Colloid and Interface Science 302:54-61 (2006).
Majumder M. et al., "Voltage Gated Carbon Nanotube Membranes", Langmuir 23(16):8624-8631 (2007).
Sun L. et al., "Single Carbon Nanotube Membranes: A Well-Defined Model for Studying Mass Transport Through Nanoporous Materials", J. Am. Chem. Soc. 122(49):12340-12345 (2000).

* cited by examiner

US 10,392,272 B2

MODULATION OF ION TRANSPORT IN A LIQUID BY APPLICATION OF AN ELECTRIC POTENTIAL ON A MESOPOROUS CARBON MEMBRANE

This invention was made with government support under Prime Contract No. DE-AC05-00OR22725 awarded by the U.S. Department of Energy. The government has certain rights in the invention.

FIELD OF THE INVENTION

The present invention relates to the field of mesoporous carbon materials, and more particularly, to mesoporous carbon materials and films, and their use in water purification, such as in methods for desalination.

BACKGROUND OF THE INVENTION

Mesoporous carbon materials have found an increasing number of utilities, most notably in water purification. In water purification, particularly desalination, mesoporous carbon materials have been applied as electrode materials in capacitive deionization (CDI) processes. When operated, i.e., by applying a suitable voltage bias across the electrodes, the CDI device removes salt species from the water by absorbing cationic species into the negatively charged electrode and anionic species into the positively charged electrode.

However, CDI technology for water purification suffers from several drawbacks that present significant obstacles to its widespread use. In particular, CDI technology generally requires appreciable voltages above 1 volt, and operates by a two-step continuous operation of ion absorption followed by ion desorption (electrode regeneration), the latter of which amounts to an additional energy burden. Particularly with the view of practicing desalination cost effectively and on a large scale, there would be a particular benefit in a water purification method with lower voltage requirement and without requiring a regeneration step.

SUMMARY OF THE INVENTION

The instant disclosure is foremost directed to a method for regulating ion transport between first and second regions of an ion-containing liquid solution partitioned by an electrically conductive mesoporous carbon membrane on which an electric potential (voltage) is applied. The method disclosed herein represents a significant advance over CDI technology for at least the reasons that the method can operate at significantly lower voltages (e.g., lower than 1 volt) and does not require a regeneration step since the membrane does not function by absorbing (or adsorbing) the ionic species. In contrast to CDI technology, the method described herein can operate by use of only a single membrane (i.e., not a two-electrode system) that functions by hindering or blocking the transport of ions instead of absorbing the ions.

In particular embodiments, the method involves applying a voltage on an electrically conductive mesoporous carbon membrane situated between first and second regions of a liquid solution, wherein ionic species are contained in at least one of the first and second regions, and wherein liquid flow between the first and second regions is permitted only through the mesoporous carbon membrane. In the method, the applied voltage is selected to modulate the degree of ion transport between the first and second regions, wherein an increase in applied voltage results in a reduction in the degree of ion transport between the first and second regions, optionally up to a critical voltage at which ion transport across the membrane ceases. The instant disclosure is also directed to the mesoporous carbon material used in the method.

BRIEF DESCRIPTION OF THE DRAWINGS

FIG. 1A is an illustration depicting a mesoporous carbon membrane on an aluminum support showing no dye transport (where dye molecules are depicted as single gray spheres) when a voltage (V) is applied to the membrane. FIG. 1B is an electron microscope image of the mesoporous carbon-carbon black (MC-CB) membrane to further elucidate the pore structure. Although not shown, in the absence of the voltage, dye molecules diffuse through the membrane.

FIG. 2A shows nitrogen adsorption isotherms for the MC-CB membrane shown in FIGS. 1A and 1B, where the amount of carbon black (CB) is varied from 0% ("OMC") to 25% ("MC-CB-25") to 50% ("MC-CB-50") to 75% ("MC-CB-75"). FIG. 2B shows pore size distribution plots for the aforesaid MC-CB composite membranes varying in the level of carbon black.

FIG. 7A is a graph showing conductivity of a receiver D.I. solution situated across a 1 mM KCl source solution at different applied voltages on the membrane, with same set up as depicted in FIGS. 3A and 3B. The conductivity results quantify the level of diffusion of the salt through the membrane. FIG. 7B is a graph showing the conductivity of the receiver D.I. solution as the voltage is changed over time.

DETAILED DESCRIPTION OF THE INVENTION

Figures 1A, 1B:
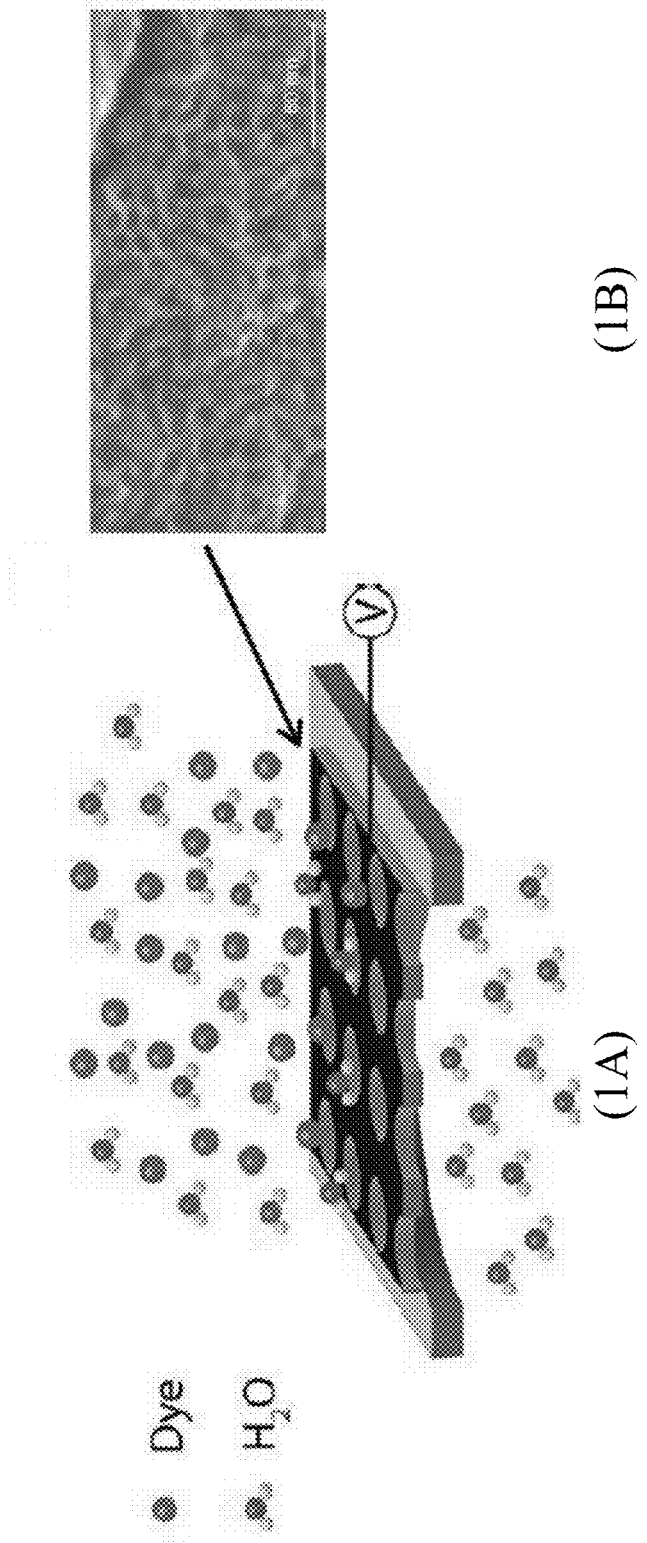
FIGS. 1A, 1B.

The mesoporous carbon membrane should be sufficiently electrically conductive so as to carry a voltage suitable for ion transport modulation or blockage in a liquid solution. As used herein, the term "membrane" indicates a shape in which one dimension (i.e., thickness) is significantly smaller than the remaining two dimensions, i.e., a film shape. Generally, so as to minimally hinder the flow of liquid through the membrane, the membrane generally has a thickness of up to or less than 1000 microns (i.e., 1000 µm, or 1 mm). Nevertheless, in order for the membrane to possess sufficient robustness, the membrane generally has a thickness of at least or above 0.1 micron (100 nm). In different embodiments, the membrane may have a thickness of at least, above, up to, or less than, for example, 100 nm (0.1 micron), 200 nm, 500 nm, 1000 nm (1 µm), 5 µm, 10 µm, 20 µmm, 30 µm, 40 µm, 50 µm, 60 µm, 70 µm, 80 µm, 90 µm, 100 µmm, 110 µmm, 120 µmm, 130 µmm, 140 µm, 150 µmm, 200 µm, 250 µmm, 300 µmm, 350 µmm, 400 µmm, 450 µmm, 500 µmm, 600 µmm, 700 µm, 800 µmm, 900 µm, or 1000 µm, or a thickness within a range bounded by any two of the foregoing exemplary values.

In some embodiments, the mesoporous carbon membrane is employed as a monolithic structure, i.e., without being part of a layered composite material. In other embodiments, the mesoporous carbon membrane may be a part of a layered composite material, wherein the mesoporous carbon membrane either overlays, underlies, or is sandwiched between one or more layers of another material compatible with the ion transport regulation process described herein. The one or more layers may function, for example, as a housing or protective device. The one or more layers can be composed of, for example, a metal or metal alloy, carbon, a metal oxide (e.g., silica, alumina, or quartz), or an organic, inorganic, or hybrid polymer, or combination thereof. The one or more layers of another material should include one or more flow-through features to permit liquid to flow across the mesoporous carbon membrane. The one or more layers of another material may, for example, be porous by having a multiplicity of flow-through features, or it may contain a single flow-through feature, i.e., a window.

As used herein and as understood in the art, the term "mesoporous", in reference to the mesoporous carbon membrane, indicates a material containing "mesopores", which are pores having a diameter (i.e., pore size) of 2 to 50 nm. In different embodiments, the mesopores can have a size of precisely or about, for example, 2, 5, 8, 10, 12, 15, 18, 20, 25, 30, 35, 40, 45, or 50 nm, or a size within a range bounded by any two of the foregoing values. As used herein, the term "about" generally indicates within ±0.5%, 1%, 2%, 5%, or up to ±10% of the indicated value. For example, a pore size of "about 10 nm" generally indicates, in its broadest sense, 10 nm ±10%, which indicates 9.0-11.0 nm. In some embodiments, the mesoporous carbon membrane contains only mesopores (i.e., 100% pore volume attributed to mesopores), while in other embodiments, the mesoporous carbon membrane includes mesopores and micropores, or mesopores and macropores, or a combination of mesopores, micropores, and macropores.

In some embodiments, micropores are present in the mesoporous carbon membrane. As used herein and as understood in the art, the term "micropores" refers to pores having a size less than 2 nm. In different embodiments, the micropores can have a size of precisely, about, up to, or less than, for example, 0.1, 0.2, 0.5, 0.8, 1, 1.2, 1.5, 1.8, or 2 nm, or a size within a range bounded by any two of the foregoing values. In different embodiments, the pore volume attributed to micropores is about, up to, less than, at least, or above, for example, 1%, 2%, 5%, 10%, 15%, 20%, 25%, 30%, 35%, 40%, 45%, 50%, 55%, 60%, 65%, or 70% of the total pore volume, or a pore volume within a range bounded by any two of the foregoing values. In other embodiments, the mesoporous carbon membrane possesses a substantial absence of micropores, which may correspond to a pore volume attributed to micropores of up to or less than 1%, 0.5%, or 0.1% with respect to the total pore volume, which includes the possibility that the mesoporous carbon membrane possesses a complete absence of micropores (i.e., 0%).

In some embodiments, macropores are present in the mesoporous carbon membrane. As used herein and as understood in the art, the term "macropores" refers to pores having a size greater than 50 nm. In some embodiments, macropores may be desirable, whereas in other embodiments, macropores may be not desirable. In different embodiments, the macropores can have a size of at least or greater than 50 nm, 60 nm, 65 nm, 70 nm, 75 nm, 80 nm, 85 nm, 90 nm, 95 nm, 100 nm, 120 nm, 150 nm, 180 nm, or 200 nm, or a size within a range bounded by any two of the foregoing values. Generally, the macropores, if present, are not present in a substantial amount. In different embodiments, the pore volume attributed to macropores is about, up to, or less than, for example, 1%, 2%, 5%, 10%, 15%, or 20% of the total pore volume, or a pore volume within a range bounded by any two of the foregoing values. In some embodiments, the mesoporous carbon membrane possesses a substantial absence of macropores, which may correspond to a pore volume attributed to macropores of up to or less than 1%, 0.5%, or 0.1% with respect to the total pore volume, which includes the possibility that the mesoporous carbon membrane possesses a complete absence of macropores (i.e., 0%).

In some embodiments, the mesoporous carbon membrane possesses a monomodal pore size distribution. A distribution (or "mode") of pores is generally defined by a single pore size of maximum (peak) pore volume concentration, i.e., "peak pore volume". In the case of a monomodal pore size distribution, the pore size distribution may, in a first instance, be defined by minimum and maximum pore sizes only in the mesopore size range, with a peak pore volume also in the mesopore size range. In a second embodiment, the monomodal pore size distribution may be defined by a minimum pore size in the micropore size range and a maximum pore size in the mesopore size range, with a peak pore volume either in the micropore size range or mesopore size range. In a third embodiment, the monomodal pore size distribution may be defined by a minimum pore size in the mesopore size range and a maximum pore size in the macropore size range, with a peak pore volume either in the mesopore size range or macropore size range. In a fourth embodiment, the monomodal pore size distribution may be defined by a minimum pore size in the micropore size range and a maximum pore size in the macropore size range, with a peak pore volume in either the micropore size range, mesopore size range, or macropore size range.

In some embodiments, the mesoporous carbon membrane possesses a bimodal, trimodal, or higher modal pore size distribution, which can be identified by the presence of, respectively, two, three, or a higher number of peak volume concentrations. In the case of a bimodal pore size distribution, the pore size distribution may, in a first instance, be defined by minimum and maximum pore sizes only in the mesopore size range, with two peak pore volumes also in the mesopore size range. In a second embodiment, the bimodal pore size distribution may be defined by a minimum pore size in the micropore size range and a maximum pore size in the mesopore size range, wherein one peak pore volume may be in the mesopore size range and the other peak pore volume in the micropore size range, or the two peak pore volumes may both be either in the micropore size range or in the mesopore size range. In a third embodiment, the bimodal pore size distribution may be defined by a minimum pore size in the mesopore size range and a maximum pore size in the macropore size range, wherein one peak pore volume may be in the mesopore size range and the other peak pore volume in the macropore size range, or the two peak pore volumes may both be either in the mesopore size range or in the macropore size range. In a fourth embodiment, the bimodal pore size distribution may be defined by a minimum pore size in the micropore size range and a maximum pore size in the macropore size range, wherein one peak pore volume may be in the mesopore size range and the other peak pore volume in the micropore size range or macropore size range, or the two peak pore volumes may both be either in the micropore size range, the mesopore size range, or in the macropore size range.

For pores that are circular or substantially circular pores, the pore size refers to the diameter of the pore. For pores that are substantially unsymmetrical or irregularly shaped, the pore size generally refers to either the average of the pore dimensions for a particular pore, or to the average or longest dimension of such pores averaged over a population of such pores. The wall thickness of mesopores is generally within the range of about 5-10 nm, e.g., 5, 5.5, 6, 6.5, 7, 7.5, 8, 8.5, 9, 9.5, or 10 nm, but may also be greater than 10 nm, such as 12 nm, 15 nm, 18 nm, 20 nm, 25 nm, 30 nm, 35 nm, 40 nm, 45 nm, or 50 nm, or within a range bounded by any two of these values.

The pores of the mesoporous carbon membrane can also possess a level of uniformity, generally either in pore diameter, pore shape, and/or pore interspacing. In particular embodiments, the pores of the mesoporous carbon membrane may possess an average pore size corresponding to any of the pore sizes exemplified above, subject to a degree of variation of no more than, for example, ±10 nm, ±8 nm, ±6, nm, ±5 nm, ±4 nm, ±3 nm, ±2 nm, ±1 nm, or ±0.5 nm. Moreover, with respect to the pore interspacing, in some embodiments, the pores may be arranged relative to each other with a certain degree of order. Some examples of ordered arrangements include a hexagonal or cubic arrangement.

In some embodiments, the mesoporous carbon membrane contains conductive carbon nanoparticles embedded therein, i.e., embedded within the continuous carbon matrix that functions as the scaffold material of the mesoporous carbon membrane. The conductive carbon nanoparticles are any of the carbon particles known in the art that are conductive, generally by virtue of a graphitic structure, and are nanosized in at least one, two, or all three of their size dimensions. Some examples of conductive carbon nanoparticles include carbon black ("CB"), carbon onion ("CO"), the spherical fullerenes (e.g., buckminsterfullerene, i.e., $C_{60}$, as well as any of the smaller or larger buckyballs, such as $C_{20}$ or $C_{70}$), the tubular fullerenes (e.g., single-walled, double-walled, or multi-walled carbon nanotubes), carbon nanodiamonds, and carbon nanobuds, all of which have compositions and physical and electrical properties well-known in the art. For purposes of the instant invention, when a carbon black is used, it is a conductive carbon black, such as an acetylene black. In the case of carbon nanodiamonds, these are generally electronic insulators and good thermal conductors, unless they are thermally treated above 1000° C., under which condition a graphitization process begins from the outer layers to the interior of the nanodiamond particles. Nanodiamonds with a graphitic outer shell are electronic conductors. As known in the art, fully graphitized carbon nanodiamonds can be considered to be carbon onions. In some embodiments, the carbon nanoparticles are not hollow, and thereby, cannot function as pores in the carbon membrane. In such an embodiment, carbon nanotubes are excluded from the carbon membrane.

The term "nanosized" or "nanosize" as used herein, in reference to the conductive carbon nanoparticles, refers to a size in at least one or two dimensions of less than 1 micron, and more typically, a size up to or less than 500 nm, 250 nm, or 100 nm. In some embodiments, all three dimensions of the nanoparticle are nanosized. In different embodiments, the conductive carbon nanoparticles have a uniform or average particle size of precisely, about, up to, or less than, for example, 1 nm, 2 nm, 5 nm, 10 nm, 20 nm, 30 nm, 40 nm, 50 nm, 100 nm, 150 nm, 200 nm, 250 nm, 300 nm, 350 nm, 400 nm, 450 nm, or 500 nm, or a size within a range bounded by any two of the foregoing values, or between any of the foregoing values and less than 1 micron. The exemplary sizes given above for nanoparticles may refer to primary or secondary (agglomerated) particle sizes, except that for purposes of the instant invention a secondary particle size also generally remains under 1 micron. Particularly when any of the exemplary sizes provided above refer to an average size, there is the possibility that a minor portion (i.e., less than 1, 2, or 5% by total weight) of carbon particles having a size greater than 1 micron may be present. However, preferably, the conductive carbon particles do not include particles having a size of 1 micron or greater. In embodiments where less than all three size dimensions are nanosized, the remaining one or two size dimensions can have a size up to or less than, for example, 2 microns, 5 microns, 10 microns, 25 microns, 50 microns, 100 microns, 250 microns, 500 microns, or 1000 microns (1 mm). The carbon nanoparticles may also be porous or non-porous. When carbon particles are included, the mesopores in the mesoporous carbon membrane are either within the mesoporous carbon matrix surrounding the carbon nanoparticles, or the mesopores are spacings delineated by surfaces of the conductive carbon nanoparticles when the conductive carbon nanoparticles are bonded with each other, or both.

By being "embedded" in the mesoporous carbon matrix is meant that the conductive carbon nanoparticles are at least coated with the mesoporous carbon matrix. The coated conductive carbon nanoparticles are separated from each other by the mesoporous carbon matrix, wherein the separation distance (matrix interspacing) can be miniscule, i.e., as a coating (e.g., up to 0.5, 1, 2, 5, or 10 nm), intermediate (e.g., greater than 10 nm, and up to 50 nm, 100 nm, or 200 nm), or substantial (e.g., greater than 200 nm, and up to 500 nm, 1 micron, 10 microns, 50 microns, 100 microns, 500 microns, or 1 mm).

In some embodiments, the conductive carbon nanoparticles are made exclusively of carbon, while in other embodiments, the conductive carbon nanoparticles can include an amount of one or a combination of non-carbon non-hydrogen (i.e., hetero-dopant) elements, such as nitrogen, oxygen, sulfur, boron, phosphorus, or a metal, such as an alkali metal (e.g., lithium), alkaline earth metal, transition metal, main group metal (e.g., Al, Ga, or In), or rare earth metal, as long as the conductive carbon nanoparticles remain substantially conductive (i.e., on the order of graphite, or useful as an electrode material), and as long as the presence of one or more hetero elements does not substantially obviate the resulting mesoporous carbon membrane from functioning according to its intended use. The amount of hetero element can be a minor amount (e.g., up to 0.1, 0.5, 1, 2, or 5 wt % or mol %) or a more substantial amount (e.g., about, at least, or up to 10, 15, 20, 25, 30, 40, or 50 wt % or mol %). In some embodiments, any one or more of the specifically recited classes or specific types of carbon nanoparticles or any one or more of the specifically recited classes or specific types of hetero-dopant elements are excluded from the carbon nanoparticles, the matrix, or the mesoporous carbon membrane altogether. Generally, the conductive carbon nanoparticles have a graphite structure or partial graphite structure, but non-graphitic conductive carbon structures, such as a conductive metal carbide (e.g., SiC and WC) are also included herein.

In some embodiments, the mesoporous carbon membrane contains conductive carbon nanoparticles surrounded by intermediate or substantial interspacings of the mesoporous carbon matrix, and all mesopores of the mesoporous carbon membrane are attributed to mesopores in the mesoporous carbon matrix. Mesopores contained within the mesoporous carbon matrix have pore walls and pore-pore interspacings constructed of the carbon matrix (scaffold) material. In other embodiments, for any of the matrix interspacings considered above (and particularly for miniscule and intermediate interspacings), the mesoporous carbon membrane contains a portion of mesopores within the mesoporous carbon matrix and a portion of mesopores completely or substantially delineated by surfaces of closely interconnected (bonded) carbon nanoparticles. Mesopores delineated by surfaces of bonded carbon nanoparticles have pore walls constructed of carbon nanoparticles coated with carbon matrix material. Thus, the mesopores are present in at least the mesoporous carbon matrix, and may also be present as spacings delineated by surfaces of the conductive carbon nanoparticles when the conductive carbon nanoparticles are bonded or fused with each other. A mesoporous carbon membrane containing a higher content of carbon nanoparticles will generally contain a greater number of mesopores delineated by surfaces of bonded carbon nanoparticles compared to a mesoporous carbon membrane containing a lower content of carbon nanoparticles. In some embodiments, a mesoporous carbon membrane containing a low enough content of carbon nanoparticles does not possess mesopores delineated by surfaces of bonded carbon nanoparticles.

Generally, the mesoporous carbon membrane may possesses a BET surface area of about or at least 50, 100, 200, 300, 400, 450, 500, 550, 600, 650, 700, 750, or 800 m$^2$/g, or a surface area within a range bounded by any two of these values. The mesoporous carbon membrane may also possess a pore volume of about or at least, for example, 0.2, 0.25, 0.3, 0.35, 0.4, 0.45, 0.5, 0.55, 0.6, 0.65, or 0.7 cm$^3$/g, or a pore volume within a range bounded by any two of these values.

In some embodiments, at least a portion or all of the mesoporous carbon matrix is non-graphitic, such as amorphous, glassy, or vitreous carbon. Generally, an amorphous portion of the carbon material includes micropores, whereas micropores are generally absent from graphitic portions. In particular embodiments, the mesoporous carbon matrix is no more than, or less than, 70%, 60%, 50%, 40%, 25%, 20%, 15%, 10%, 5%, 2%, or 1% graphitic, or a percentage therebetween. In some embodiments, all (e.g., about or precisely 100%) or substantially all (for example, greater than 90%, 95%, 98%, or 99%) of the porous carbon material is non-graphitic, and may be instead, for example, amorphous or glassy carbon.

In another aspect, the invention is directed to a method for fabricating the conductive mesoporous carbon membrane described above. The method first involves providing (i.e., preparing or otherwise obtaining in prepared form) a precursor composition, which is subsequently subjected to a curing step followed by a carbonization step in order to produce the mesoporous carbon composite described above. The precursor composition includes at least the following components: (i) a templating component containing one or more block copolymers, (ii) one or more phenolic compounds or materials (i.e., "phenolic component"), (iii) one or more crosslinkable aldehyde compounds or materials (i.e., "aldehyde component"), (iv) an acid catalyst, and optionally, (v) conductive carbon nanoparticles. The combination of phenolic component and aldehyde component is herein referred to as the "carbon precursor" or "polymer precursor" or "polymer precursor components". The resulting polymer produced from the polymer precursor (i.e., after polymerization and crosslinking of phenolic and aldehyde components) functions as the carbon precursor, which is converted to carbon during a carbonization step. In contrast, the templating component (i.e., block copolymer) functions to organize the polymer precursor materials in an ordered (i.e., patterned) arrangement before the carbonization step. During carbonization, the block copolymer is generally completely volatized into gaseous byproducts, and thereby, generally does not contribute to formation of the solid carbon matrix. However, the volatile gases produced from the block copolymer serve the important role of creating mesopores (and sometimes micropores) in the carbon matrix during the carbonization step. During carbonization, the carbon precursor components (i.e., phenolic and aldehyde components), along with templating component, together produce the mesoporous carbon matrix. If conductive carbon nanoparticles are included with the precursor and template, they become embedded in the resulting carbon matrix.

The templating component considered herein generally contains one or more block copolymers. As used herein, a "block copolymer" is a polymer containing two or more chemically distinct polymeric blocks (i.e., sections or segments). The copolymer can be, for example, a diblock copolymer (e.g., A-B), triblock copolymer (e.g., A-B-C), tetrablock copolymer (e.g., A-B-C-D), or higher block copolymer, wherein A, B, C, and D represent chemically distinct polymeric segments. The block copolymer is typically not completely inorganic, and is more typically completely organic (i.e., carbon-based) in order that the block copolymer is at least partially capable of volatilizing during the carbonization step. Preferably, the block copolymer contains at least two segments that possess a difference in hydrophilicity or hydrophobicity (i.e., is amphiphilic). Such block copolymers typically form periodic structures by virtue of selective interactions between like domains, i.e., between hydrophobic domains and between hydrophilic domains. The block copolymer is typically linear; however, branched (e.g., glycerol branching units) and grafted block copolymer variations are also contemplated herein. Preferably, the block copolymer contains polar groups capable of interacting (e.g., by hydrogen or ionic bonding) with the phenolic compound or material. For this reason, the block copolymer is preferably not a complete hydrocarbon such as styrene-butadiene. Some of the groups preferably located in the block copolymer which can provide a favorable interactive bond with phenol groups include, for example, hydroxy, amino, imino, and carbonyl groups.

Some general examples of suitable classes of block copolymers include those containing segments of polyacrylate or polymethacrylate (and esters thereof), polystyrene, polyethyleneoxide, polypropyleneoxide, polyethylene, polyacrylonitrile, polylactide, and polycaprolactone. Some specific examples of suitable block copolymers include polystyrene-b-poly(methylmethacrylate) (i.e., PS-PMMA), polystyrene-b-poly(acrylic acid) (i.e., PS-PAA), polystyrene-b-poly(4-vinylpyridine) (i.e., PS-P4VP), polystyrene-b-poly(2-vinylpyridine) (i.e., PS-P2VP), polyethylene-b-poly(4-vinylpyridine) (i.e., PE-P4VP), polystyrene-b-polyethyleneoxide (i.e., PS-PEO), polystyrene-b-poly(4-hydroxystyrene), polyethyleneoxide-b-polypropyleneoxide (i.e., PEO-PPO), polyethyleneoxide-b-poly(4-vinylpyridine) (i.e., PEO-P4VP), polyethylene-b-polyethyleneoxide (i.e., PE-PEO), polystyrene-b-poly(D,L-lactide), polystyrene-b-poly(methylmethacrylate)-b-polyethyleneoxide (i.e., PS-PMMA-PEO), polystyrene-b-polyacrylamide, polystyrene-b-polydimethylacrylamide (i.e., PS-PDMA), polystyrene-b-polyacrylonitrile (i.e., PS-PAN), and polyethyleneoxide-b-polyacrylonitrile (i.e., PEO-PAN).

In a particular embodiment, the block copolymer is a triblock copolymer containing one or more poly-EO segments and one or more poly-PPO segments. More preferably, the triblock copolymer is a poloxamer (i.e. Pluronic® or Lutrol® polymer) according to the general formula

$$(PEO)_a\text{-}(PPO)_b\text{-}(PEO)_c \qquad (1)$$

In Formula (1), PEO is a polyethylene oxide block and PPO is a polypropylene block (i.e., —$CH_2CH(CH_3)O$— or —$CH(CH_3)CH_2O$—), and the subscripts a, b, and c represent the number of monomer units of PEO and PPO, as indicated. Typically, a, b, and c in Formula (1) are each at least 2, and more typically, at least 5, and typically up to a value of 100, 120, or 130. Subscripts a and c are typically of equal value in these types of polymers. In different embodiments, a, b, and c can independently have a value of about, or at least, or up to 10, 20, 30, 40, 50, 60, 70, 80, 90, 100, 120, 130, 140, 150, 160, 180, 200, 220, 240, or any particular range established by any two of these exemplary values.

In one embodiment, a and c values in Formula (1) are each less than b, i.e., the hydrophilic PEO block is shorter on each end than the hydrophobic PPO block. For example, in different embodiments, a, b, and c can each independently have a value of 2, 5, 7, 10, 12, 15, 20, 25, 30, 35, 40, 45, 50, 55, 60, 65, 70, 75, 80, 85, 90, 95, 100, 110, 120, 130, 140, 150, or 160, or any range delimited by any two of these values, provided that a and c values are each less than b. Furthermore, in different embodiments, it can be preferred for the a and c values to be less than b by a certain number of units, e.g., by 2, 5, 7, 10, 12, 15, 20, 25, 30, 35, 40, 45, or 50 units, or any range therein. Alternatively, it can be preferred for the a and c values to be a certain fraction or percentage of b (or less than or greater than this fraction or percentage), e.g., about 10%, 20%, 25%, 30, 33%, 40%, 50%, 60%, 70%, 75%, 80%, 85%, 90%, or any range delimited by any two of these values.

In another embodiment, a and c values in Formula (1) are each greater than b, i.e., the hydrophilic PEO block is longer on each end than the hydrophobic PPO block. For example, in different embodiments, a, b, and c can each independently have a value of 2, 5, 7, 10, 12, 15, 20, 25, 30, 35, 40, 45, 50, 55, 60, 65, 70, 75, 80, 85, 90, 95, 100, 110, 120, 130, 140, 150, or 160, or any range delimited by any two of these values, provided that a and c values are each greater than b. Furthermore, in different embodiments, it can be preferred for the a and c values to be greater than b by a certain number of units, e.g., by 2, 5, 7, 10, 12, 15, 20, 25, 30, 35, 40, 45, or 50 units, or any range therein. Alternatively, it can be preferred for the b value to be a certain fraction or percentage of a and c values (or less than or greater than this fraction or percentage), e.g., about 10%, 20%, 25%, 30, 33%, 40%, 50%, 60%, 70%, 75%, 80%, 85%, 90%, or any range delimited by any two of these values.

In different embodiments, the poloxamer preferably has a minimum average molecular weight of at least 500, 800, 1000, 1200, 1500, 2000, 2500, 3000, 3500, 4000, or 4500 g/mole, and a maximum average molecular weight of 5000, 5500, 6000, 6500, 7000, 7500, 8000, 8500, 9000, 9500, 10,000, 12,000, 15,000, or 20,000 g/mole, wherein a particular range can be established between any two of the foregoing values, and particularly, between any two of the minimum and maximum values provided. The viscosity of the polymers is generally at least 200, 250, 300, 350, 400, 450, 500, 550, 600, or 650 centipoise (cps), and generally up to 700, 800, 900, 1000, 1500, 2000, 2500, 3000, 3500, 4000, 4500, 5000, 5500, 6000, 6500, 7000, or 7500 cps, or any particular range established between any two of the foregoing values.

The following table lists several exemplary poloxamer polymers applicable to the present invention.

TABLE 1

Some exemplary poloxamer polymers

| Generic Name | Pluronic ® Name | Approximate value of a | Approximate value of b | Approximate value of c |
|---|---|---|---|---|
| Poloxamer 101 | Pluronic L-31 | 2 | 16 | 2 |
| Poloxamer 105 | Pluronic L-35 | 11 | 16 | 11 |
| Poloxamer 108 | Pluronic F-38 | 46 | 16 | 46 |
| Poloxamer 122 | — | 5 | 21 | 5 |
| Poloxamer 123 | Pluronic L-43 | 7 | 21 | 7 |
| Poloxamer 124 | Pluronic L-44 | 11 | 21 | 11 |
| Poloxamer 181 | Pluronic L-61 | 3 | 30 | 3 |
| Poloxamer 182 | Pluronic L-62 | 8 | 30 | 8 |
| Poloxamer 183 | — | 10 | 30 | 10 |
| Poloxamer 184 | Pluronic L-64 | 13 | 30 | 13 |
| Poloxamer 185 | Pluronic P-65 | 19 | 30 | 19 |
| Poloxamer 188 | Pluronic F-68 | 75 | 30 | 75 |
| Poloxamer 212 | — | 8 | 35 | 8 |
| Poloxamer 215 | — | 24 | 35 | 24 |
| Poloxamer 217 | Pluronic F-77 | 52 | 35 | 52 |
| Poloxamer 231 | Pluronic L-81 | 6 | 39 | 6 |
| Poloxamer 234 | Pluronic P-84 | 22 | 39 | 22 |
| Poloxamer 235 | Pluronic P-85 | 27 | 39 | 27 |
| Poloxamer 237 | Pluronic F-87 | 62 | 39 | 62 |
| Poloxamer 238 | Pluronic F-88 | 97 | 39 | 97 |
| Poloxamer 282 | Pluronic L-92 | 10 | 47 | 10 |
| Poloxamer 284 | — | 21 | 47 | 21 |
| Poloxamer 288 | Pluronic F-98 | 122 | 47 | 122 |
| Poloxamer 331 | Pluronic L-101 | 7 | 54 | 7 |
| Poloxamer 333 | Pluronic P-103 | 20 | 54 | 20 |
| Poloxamer 334 | Pluronic P-104 | 31 | 54 | 31 |
| Poloxamer 335 | Pluronic P-105 | 38 | 54 | 38 |
| Poloxamer 338 | Pluronic F-108 | 128 | 54 | 128 |
| Poloxamer 401 | Pluronic L-121 | 6 | 67 | 6 |
| Poloxamer 403 | Pluronic P-123 | 21 | 67 | 21 |
| Poloxamer 407 | Pluronic F-127 | 98 | 67 | 98 |

As known in the art, the names of the poloxamers and Pluronics (as given above) contain numbers which provide information on the chemical composition. For example, the generic poloxamer name contains three digits, wherein the first two digits×100 indicates the approximate molecular weight of the PPO portion and the last digit×10 indicates the weight percent of the PEO portion. Accordingly, poloxamer 338 possesses a PPO portion of about 3300 g/mole molecular weight, and 80 wt % PEO. In the Pluronic name, the letter indicates the physical form of the product, i.e., L=liquid, P=paste, and F=solid, i.e., flake. The first digit, or two digits for a three-digit number, multiplied by 300, indicates the approximate molecular weight of the PPO portion, while the last digit×10 indicates the weight percent of the PEO portion. For example, Pluronic® F-108 (which corresponds to poloxamer 338) indicates a solid form composed of about 3,000 g/mol of the PPO portion and 80 wt % PEO.

Numerous other types of copolymers containing PEO and PPO blocks are possible, all of which are applicable herein. For example, the block copolymer can also be a reverse poloxamer of general formula:

 (2)

wherein all of the details considered above with respect to the regular poloxamers (e.g., description of a, b, and c subscripts, and all of the other exemplary structural possibilities) are applicable by reference herein to the reverse poloxamers.

In another variation, the block copolymer contains a linking diamine group (e.g., ethylenediamine, i.e., EDA) or triamine group (e.g., melamine). Some examples of such copolymers include the Tetronics® (e.g., PEO-PPO-EDA-PPO-PEO) and reverse Tetronics® (e.g., PPO-PEO-EDA-PEO-PPO).

In some embodiments, any one or more classes or specific types of block copolymers described above are excluded from the preparative method described herein.

The phenolic compound or material of the precursor composition can be any phenolic compound or material that can react by a condensation reaction with an aldehydic compound or material (such as formaldehyde) under acidic conditions. Typically, any compound or material containing a hydroxy group bound to an aromatic ring (typically, a phenyl ring) is suitable for the present invention as a phenolic compound or material.

In one embodiment, the phenolic compound or material contains one hydroxy group bound to a benzene ring. The benzene ring may be unsubstituted (i.e., the compound "phenol"), or the benzene ring may be substituted with one or more groups, such as one or more groups selected from hydrocarbon, halide, nitro, amino, hydroxy, and alkoxy groups. Some examples of such compounds include phenol, the halophenols, the aminophenols, the hydrocarbyl-substituted phenols (wherein "hydrocarbyl" includes, e.g., straight-chained, branched, or cyclic alkyl, alkenyl, or alkynyl groups typically containing from 1 to 6 carbon atoms, optionally substituted with one or more oxygen or nitrogen atoms), naphthols, nitrophenols, hydroxyanisoles, hydroxybenzoic acids, fatty acid ester-substituted or polyalkyleneoxy-substituted phenols (e.g., on the 2 or 4 positions with respect to the hydroxy group), phenols containing an azo linkage (e.g., p-hydroxyazobenzene), phenolsulfonic acids (e.g., p-phenolsulfonic acid), and dihydroxybiphenyls. Some general subclasses of halophenols include the fluorophenols, chlorophenols, bromophenols, and iodophenols, and their further sub-classification as, for example, p-halophenols (e.g., 4-fluorophenol, 4-chlorophenol, 4-bromophenol, and 4-iodophenol), m-halophenols (e.g., 3-fluorophenol, 3-chlorophenol, 3-bromophenol, and 3-iodophenol), o-halophenols (e.g., 2-fluorophenol, 2-chlorophenol, 2-bromophenol, and 2-iodophenol), dihalophenols (e.g., 3,5-dichlorophenol and 3,5-dibromophenol), and trihalophenols (e.g., 3,4,5-trichlorophenol, 3,4,5-tribromophenol, 3,4,5-trifluorophenol, 3,5,6-trichlorophenol, and 2,3,5-tribromophenol). Some examples of aminophenols include 2-, 3-, and 4-aminophenol, and 3,5- and 2,5-diaminophenol. Some examples of nitrophenols include 2-, 3-, and 4-nitrophenol, and 2,5- and 3,5-dinitrophenol. Some examples of hydrocarbyl-substituted phenols include the cresols, i.e., methylphenols or hydroxytoluenes (e.g., o-cresol, m-cresol, p-cresol), the xylenols (e.g., 3,5-, 2,5-, 2,3-, and 3,4-dimethylphenol), the ethylphenols (e.g., 2-, 3-, and 4-ethylphenol, and 3,5- and 2,5-diethylphenol), n-propylphenols (e.g., 4-n-propylphenol), isopropylphenols (e.g., 4-isopropylphenol), butylphenols (e.g., 4-n-butylphenol, 4-isobutylphenol, 4-t-butylphenol, 3,5-di-t-butylphenol, 2,5-di-t-butylphenol), hexylphenols, octyl phenols (e.g., 4-n-octylphenol), nonylphenols (e.g., 4-n-nonylphenol), phenylphenols (e.g., 2-phenylphenol, 3-phenylphenol, and 4-phenylphenol), and hydroxycinnamic acid (p-coumaric acid). Some examples of hydroxyanisoles include 2-methoxyphenol, 3-methoxyphenol, 4-methoxyphenol, 3-t-butyl-4-hydroxyanisole (e.g., BHA), and ferulic acid. Some examples of hydroxybenzoic acids include 2-hydroxybenzoic acid (salicylic acid), 3-hydroxybenzoic acid, 4-hydroxybenzoic acid, and their organic acid esters (e.g., methyl salicylate and ethyl-4-hydroxybenzoate).

In another embodiment, the phenolic compound or material contains two phenol groups (i.e. two hydroxy groups bound to a benzene ring, or two hydroxy groups bound to different benzene rings of the same molecule). Some examples of such compounds include catechol, resorcinol, hydroquinone, the hydrocarbyl-linked bis-phenols (e.g., bisphenol A, methylenebisphenol, and 4,4'-dihydroxystilbene), 4,4'-dihydroxybiphenyl (i.e., 4,4'-biphenol), the halo-substituted diphenols (e.g., 2-haloresorcinols, 3-haloresorcinols, and 4-haloresorcinols, wherein the halo group can be fluoro, chloro, bromo, or iodo), the amino-substituted diphenols (e.g., 2-aminoresorcinol, 3-aminoresorcinol, and 4-aminoresorcinol), the hydrocarbyl-substituted diphenols (e.g., 2,6-dihydroxytoluene, i.e., 2-methylresorcinol; 2,3-, 2,4-, 2,5-, and 3,5-dihydroxytoluene, 1-ethyl-2,6-dihydroxybenzene, caffeic acid, and chlorogenic acid), the nitro-substituted diphenols (e.g., 2-and 4-nitroresorcinol), dihydroxyanisoles (e.g., 3,5-, 2,3-, 2,5-, and 2,6-dihydroxyanisole, and vanillin), dihydroxybenzoic acids (e.g., 3,5-, 2,3-, 2,5-, and 2,6-dihydroxybenzoic acid, and their alkyl esters, and vanillic acid), and phenolphthalein.

In another embodiment, the phenolic compound or material contains three phenol groups (i.e. three hydroxy groups bound to a benzene ring, or three hydroxy groups bound to different benzene rings of the same molecule) . Some examples of such compounds include phloroglucinol (1,3,5-trihydroxybenzene), pyrogallol (1,2,3-trihydroxybenzene), 1,2,4-trihydroxybenzene, 5-chloro-1,2,4-trihydroxybenzene, resveratrol(trans-3,5,4'-trihydroxystilbene), the hydrocarbyl-substituted triphenols (e.g., 2,4,6-trihydroxytoluene, i.e., methylphloroglucinol, and 3,4,5-trihydroxytoluene), the halogen-substituted triphenols (e.g., 5-chloro-1,2,4-trihydroxybenzene), the carboxy-substituted triphenols (e.g., 3,4,5-trihydroxybenzoic acid, i.e., gallic acid or quinic acid, and 2,4,6-trihydroxybenzoic acid), the nitro-substituted triphenols (e.g., 2,4,6-trihydroxynitrobenzene), and phenol-formaldehyde resoles or novolak resins containing three phenol groups.

In yet another embodiment, the phenolic compound or material contains multiple (i.e., greater than three) phenol groups. Some examples of such compounds or materials include tannin (e.g., tannic acid), tannin derivatives (e.g., ellagotannins and gallotannins), phenol-containing polymers (e.g., poly-(4-hydroxystyrene)), phenol-formaldehyde resoles or novolak resins containing at least four phenol groups (e.g., at least 4, 5, or 6 phenol groups, and generally of 500-5000 M.W.), quercetin, ellagic acid, and tetraphenol ethane.

In some embodiments, any one or more classes or specific types of phenolic compounds or materials described above are excluded from the preparative method described herein.

The crosslinkable aldehyde component can be any organic compound or material containing an aldehyde group. In many embodiments, the crosslinkable aldehyde is formaldehyde. However, there are also numerous organoaldehydes, organodialdehydes, and polyaldehydes (e.g., organotrialdehydes, organotetraaldehydes, and so on) considered herein which can serve the same purpose. The organoaldehydes can be generally represented by the following formula:

In Formula (3), R can represent a straight-chained, branched, or cyclic hydrocarbyl group, which can be either saturated or unsaturated, typically containing at least 1, 2, or 3 carbon atoms, and up to 4, 5, 6, 7, or 8 carbon atoms. Some examples of suitable organoaldehydes include acetaldehyde, propanal (propionaldehyde), butanal (butyraldehyde), pentanal (valeraldehyde), hexanal, crotonaldehyde, acrolein, benzaldehyde, and furfural.

The organodialdehydes can be generally represented by the following formula:

wherein R is a bond (in the case of glyoxal) or a straight-chained, branched, or cyclic hydrocarbyl linking group, which can be either saturated or unsaturated, typically containing at least 1, 2, or 3 carbon atoms, and up to 4, 5, 6, 7, 8, 9, or 10 carbon atoms. Some examples of dialdehyde compounds include glyoxal (when R is a bond), malondialdehyde (when R is methylene), succinaldehyde, glutaraldehyde, adipaldehyde, pimelaldehyde, suberaldehyde, sebacaldehyde, cyclopentanedialdehyde, terephthaldehyde, and furfuraldehyde. In some embodiments, one of the aldehydic hydrogens of a dialdehyde can be replaced with a hydrocarbyl group, thereby resulting in an aldehyde-ketone dione compound, such as methylglyoxal or 1,3-butanedione.

In some embodiments, any one or more classes or specific types of aldehyde compounds or materials described above are excluded from the preparative method described herein.

The acidic component in the precursor composition can be any acid strong enough to accelerate the reaction between phenolic and dione compounds. In some embodiments, the acid is a weak acid, such as a weak organic acid (e.g., acetic acid, propionic acid, or citric acid) or a weak inorganic acid (e.g., phosphoric acid). In other embodiments, the acid is a strong acid, such as a mineral acid, such as hydrochloric acid, hydrobromic acid, hydroiodic acid, sulfuric acid, or a superacid, such as triflic acid. Depending on the type of acid and other conditions, the molar concentration of acid (per total precursor composition) can be, for example, precisely, about, at least, less than, or up to 0.1 molar (i.e., 0.1 M), 0.2 M, 0.5 M, 1.0 M, 1.5 M, 2.0 M, 2.5 M, 3.0 M, 3.5 M, 4.0 M, 4.5 M, 5.0M, or an acid concentration within a range bounded by any two of the foregoing values. The molar concentration values given may also be referred to in terms of molar equivalents of $H^+$, or pH, wherein the pH for a strong acid generally abides by the formula $pH=-\log[H^+]$, wherein $[H^-]$ represents the concentration of $H^+$ ions. In some embodiments, any one or more classes or specific types of acids described above are excluded from the preparative method described herein. In a particular embodiment, a weak acid (i.e., having a pKa above −2), such as weak organic acids (e.g., p-toluenesulfonic acid) or weak inorganic acids (e.g., phosphoric or hypophosphorous acid), are excluded from the precursor composition.

Any one or more of the above components or final product can be dissolved, dispersed, or otherwise in contact with a liquid, which can be a suitable solvent. The solvent can be, for example, an organic polar protic or non-protic solvent. Some examples of organic polar protic solvents include alcohols, e.g., methanol, ethanol, n-propanol, isopropanol, ethylene glycol, and the like. Some examples of organic polar non-protic solvents include acetonitrile, dimethylformamide, dimethylsulfoxide, methylene chloride, organoethers (e.g., tetrahydrofuran or diethylether), and the like. The liquid or solvent can also be an ionic liquid, such as an imidazolium or piperidinium ionic liquid. The liquid or solvent can be used in the processing of components to make the final product (and generally, eventually removed), or included with the product as a component of the final product or an intermediate thereof. In some embodiments, any one or more of the above classes or specific types of liquids can be excluded from a portion or the entire preparative process described above, or from the final product.

In some embodiments, the molar amount of crosslinkable aldehyde component is higher than the molar amount of phenolic component (i.e., molar ratio of aldehyde to phenolic components is greater than 1). In such embodiments, the molar ratio of aldehyde to phenolic components may be precisely, about, or at least, for example, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, or within a range bounded by any two of these values. In other embodiments, the molar amount of aldehyde component is less than the molar amount of phenolic component (i.e., molar ratio of aldehyde to phenolic components is less than 1). In such embodiments, the molar ratio of aldehyde to phenolic components may be precisely, about, or less than, for example, 0.9, 0.8, 0.7, 0.6, 0.5, 0.4, 0.3, or 0.2, or within a range bounded by any two of these values. In other embodiments, the molar amount of aldehyde component is about the same as the molar amount of phenolic component, i.e., a ratio of about 1.

The amount of conductive carbon nanoparticles incorporated into the composite material can be conveniently expressed as a percent by weight (wt %) of the conductive carbon nanoparticles by total weight of the carbon nanoparticles and phenolic component. Thus, if wt % of carbon nanoparticles is designated by X, the wt % of the phenolic component can be designated as 100-X. In some embodiments, the percent by weight of carbon nanoparticles by total weight of carbon nanoparticles and phenolic component is greater than zero and less than 100%. By the foregoing definition, an amount of carbon nanoparticles of 0% corresponds to an amount of phenolic component of 100%; and an amount of carbon nanoparticles of 100% corresponds to an amount of phenolic component of 0%. In different embodiments, the amount of carbon nanoparticles can be precisely, at least, up to, or less than, for example, 1 wt %, 2 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, or 97 wt % by total weight of the carbon nanoparticles and phenolic component, or a wt % of carbon nanoparticles within a range bounded by any two of the foregoing exemplary values (for example, a minimum wt % of carbon nanoparticles of 5, 10, 15, 20, 25, or 30 wt % and a maximum wt % of carbon nanoparticles of 50, 60, 70, 75, 80, 85, 90, or 95 wt %).

After the precursor components (i.e., i to iv, and optionally v) are combined and mixed, the combined mixed components are deposited as a thin film on a substrate. The precursor composition can be deposited by any suitable means known in the art to produce a film (i.e., coating) of the precursor composition on a substrate. Some examples of solution deposition processes include spin-coating, brush coating (painting), spraying, and dipping. After being deposited, the precursor film is generally subjected to a curing step to convert the mixture to a crosslinked gel or solid material. The curing step includes any of the conditions, as known in the art, that promote polymerization, and preferably, crosslinking, of polymer precursors, and in particular, crosslinking between phenolic and aldehydic components to form a solid crosslinked carbon precursor. The curing conditions generally include application of an elevated temperature for a specified period of time without significant carbonization (or any carbonization) of the precursor. Other curing conditions and methods can be used in the curing step, including radiative (e.g., UV curing) or purely chemical (i.e., without use of an elevated temperature). Preferably, the curing step involves subjecting the polymer precursors or the entire precursor composition to a temperature of about, at least, up to, or less than 60, 70, 80, 90, 100, 110, 120, 130, 140° C., 150° C., 160° C., 170° C., 180° C., 190° C., or 200° C. for a time period of, typically, at least 0.5, 1, 2, 5, 10, or 12 hours and up to 15, 20, 24, 36, 48, or 72 hours, wherein it is understood that higher temperatures generally require shorter time periods. Alternatively, the curing temperature is within a range bounded by any two of the exemplary curing temperatures recited above.

In particular embodiments, it may be preferable to subject the film precursor to an initial lower temperature curing step followed by a higher temperature curing step. The initial curing step may employ a temperature of about, for example, 60, 70, 80, 90, or 100° C. (or a range between any of these), while the subsequent curing step may employ a temperature of about, for example, 90, 100, 110, 120, 130, 140° C., 150° C., 160° C., 170° C., 180° C., 190° C., or 200° C. (or a range between any of these), provided that the temperature of the initial curing step is less than the temperature of the subsequent curing step. In addition, each curing step can employ any of the exemplary time periods given above.

Alternatively, it may be preferred to gradually increase the temperature during the curing step between any of the temperatures given above, or between room temperature (e.g., 15, 20, 25, 30, or 35° C.) and any of the temperatures given above. In different embodiments, the gradual increase in temperature can be practiced by employing a temperature increase rate of, or at least, or no more than 1° C./min, 2° C./min, 3° C./min, 5° C./min, 7° C./min, 10° C./min, 12° C./min, 15° C./min, 20° C./min, or 30° C./min, or any suitable range between any of these values. The gradual temperature increase can also include one or more periods of residency at a particular temperature, and/or a change in the rate of temperature increase.

In some embodiments, after combining the components of the precursor composition, and before depositing the precursor composition on a substrate, the solution is stirred for a sufficient period of time (e.g., at least or about 1, 2, 5, 10, 20, 30, 40, 50, 60, 90, or 120 minutes, or a range between any these values) until a phase separation or precipitation is evident. In some cases, the solution turns turbid. The turbidity generally indicates formation of an ordered nanocomposite gel or solid which has undergone a degree of phase separation from the liquid portion of the solution. If desired, stirring can be continued after the onset of turbidity, such that the total amount of stirring time before curing, carbonization, or a phase-separation process is any of the exemplary time periods given above, or a much longer period of time, such as several hours (e.g., at least or about 4, 5, 6, 7, 8, 10, or 12 hours) or days (e.g., at least or about 1, 2, 3, 4, 5, 10, 15, or 20 days), or a range between of the foregoing exemplary periods of time.

After turbidity becomes evident, the phase-separated mixture can be subjected to conditions that cause the polymerized precursor material to be isolated from the liquid portion. Any separation method can be applied herein. In a preferred embodiment, the phases are separated by centrifugation. In different embodiments, the centrifugation can be conducted at an angular speed of or at least, for example, 2000 rpm, 2500 rpm, 3000 rpm, 4000 rpm, 5000 rpm, 6000 rpm, 7000 rpm, 8000 rpm, 9000 rpm, 9500 rpm, 10000 rpm, 11000 rpm, 12000 rpm, or 15000 rpm, or a range between any of these values, for a period of time of, for example, 0.1, 0.2, 0.5, 1, 2, 3, 4, 5, 10, or 15 minutes, wherein it is understood that higher angular speeds generally require less amounts of time to effect an equivalent degree of separation. Superspeed centrifugation (e.g., up to 20,000 or 30,000 rpm) or ultracentrifugation (e.g., up to 40,000, 50,000, 60,000, or 70,000 rpm) can also be used. The gel or solid phase, once separated from the liquid phase, is preferably cured and carbonized in the substantial absence of the liquid phase according to any of the conditions described above for these processes.

In some embodiments, a multi-step process is employed in producing the precursor film. For example, a multi-step process may be employed wherein a film containing the templating component in combination with the phenolic component is first produced by, for example, applying (i.e., coating) the aforesaid mixture of components onto a surface, and casting the components as a solid film by removing solvent therefrom (e.g., by annealing). The above film may then subsequently be reacted with the crosslinkable aldehyde component (e.g., by a vapor phase reaction with, for example, formaldehyde vapor) under acidic conditions to produce the polymerized (and optionally, crosslinked) carbon precursor material. The resulting precursor film may then be cured and then carbonized to produce the mesoporous carbon membrane.

The cured film is subjected to a carbonization step to produce the mesoporous carbon membrane. The carbonization step includes any of the conditions, as known in the art, which cause carbonization of the precursor composition, and which is generally no more than or less than 2000° C. In different embodiments, a carbonization temperature of about, at least, up to, or less than, for example, 300° C., 350° C., 400° C., 450° C., 500° C., 550° C., 600° C., 650° C., 700° C., 750° C., 800° C., 850° C., 900° C., 950° C., 1000° C., 1050° C., 1100° C., 1150° C., 1200° C., 1250° C., 1300° C., 1350° C., 1400° C., 1450° C., 1500° C., 1600° C., 1700° C., 1800° C., 1900° C., or 2000° C. (or a temperature within a range therein) is employed for a time period of, typically, at least 1, 2, 3, 4, 5, or 6 hours and up to 7, 8, 9, 10, 11, or 12 hours, wherein it is understood that higher temperatures generally require shorter time periods to achieve the same result. Alternatively, the carbonization temperature may be selected from a range bounded by any two exemplary carbonization temperatures recited above.

In particular embodiments, it may be preferable to subject the precursors to an initial lower temperature carbonization step followed by a higher temperature carbonization step. The initial carbonization step may employ a temperature of about, for example, 300, 350, 400, 450, 500, 550, 600, 650, 700, 750, 800, 850, or 900° C. (or a range between any of these), while the subsequent carbonization step may employ a temperature of about, for example, 500, 550, 600, 650, 700, 750, 800, 850, 900, 950, 1000, 1050, 1100, 1200, 1250, 1300, 1400, 1450, 1500, 1600, 1700, 1900° C., or 2000° C. (or a range between any of these), provided that the temperature of the initial carbonization step is less than the temperature of the subsequent carbonization step. In addition, each carbonization step can employ any of the exemplary time periods given above.

Alternatively, it may be preferable to gradually increase the temperature during the carbonization step between any of the carbonization temperatures given above, or between room temperature (e.g., 15, 20, 25, 30, or 35° C.) or any of the curing temperatures provided above and any of the carbonization temperatures given above. Thus, in some embodiments, a curing step and carbonization step may be performed continuously, one after the other, with no clear boundary between the steps. In different embodiments, the gradual increase in temperature can be practiced by employing a temperature increase rate of, or at least, or no more than 1° C./min, 2° C./min, 3° C./min, 5° C./min, 7° C./min, 10° C./min, 12° C./min, 15° C./min, 20° C./min, 30° C./min, 40° C./min, or 50° C./min, or any suitable range between any of these values. The gradual temperature increase can also include one or more periods of residency at a particular temperature, and/or a change in the rate of temperature increase.

The mesoporous carbon membrane, after carbonization, should have an acceptable level of conductivity, particularly when conductive (generally, graphitic) carbon nanoparticles are incorporated in the mesoporous carbon membrane. Nevertheless, the mesoporous carbon material can be made more conductive by subjecting the carbon membrane to graphitization, which can be achieved at temperatures significantly higher than those employed for carbonization (e.g., above 2000° C.). Typically, the temperature capable of causing graphitization is a temperature of or greater than about 2100° C., 2200° C., 2300° C., 2400° C., 2500° C., 2600° C., 2700° C., 2800° C., 2900° C., 3000° C., 3100° C., or 3200° C., or a range bounded by any two of these temperatures. Other conditions that generally favor graphitization (e.g., inclusion of catalytic species, such as iron (III) complexes) may be included, but can also be excluded in some embodiments. Typically, the carbonization or graphitization step is conducted in an atmosphere substantially removed of oxygen, e.g., typically under an inert atmosphere, such as nitrogen or argon. In some embodiments, a graphitization step is omitted, particularly since the high temperature employed in the graphitization step may have deleterious effects, such as collapse of the mesoporous architecture.

The mesoporous carbon membrane can also be functionalized, if desired, by methods known in the art for functionalizing carbon or graphite materials. For example, the carbon membrane may be nitrogenated, fluorinated, or oxygenated by methods known in the art. The carbon membrane may be nitrogenated, fluorinated, or oxygenated, by, for example, exposure of the carbon film, either during or after the carbonization process, to ammonia, fluorine gas, or oxygen, respectively, under suitably reactive conditions. In the particular case of fluorination, the carbon material is typically placed in contact with fluorine gas for a period of several minutes (e.g., 10 minutes) up to several days at a temperature within 20° C. to 500° C., wherein the time and temperature, among other factors, are selected based on the degree of fluorination desired. For example, a reaction time of about 5 hours at ambient temperature (e.g., 15-30° C.) typically results in fluorination of about 10% of the total carbon; in comparison, fluorination conducted at about 500° C. for two days results in about 100% fluorination of the total carbon. In particular embodiments, the degree of nitrogenation, fluorination, or oxygenation can be about or at least 1%, 2%, 5%, 10%, 20%, 30%, 40%, 50%, 60%, 70%, 80%, 90%, 95%, or 100%, or a range between any two of these values. Alternatively, before conductive carbon nanoparticles are mixed with the matrix precursor, the conductive carbon nanoparticles are functionalized by any of the above methods, or with a molecular or polymeric coating. In some embodiments, molecular tethers may be attached to the surface of the carbon membrane, including pore walls, in order to, for example, improve wettability and liquid flow through the membrane. However, in some embodiments, molecular tethers are excluded from the membrane, particularly since the method described herein does not function by absorption of ionic species.

The mesoporous carbon membrane produced according to the methods described above preferably possesses a significant degree of physical resilience and robustness, such as a high thermal stability and resistance to cracking. An improved thermal stability is preferably evidenced by a substantial absence of structural shrinkage, and/or a substantial preservation of mesoporosity, and/or a substantial preservation of the BET surface area after being heat-treated at a temperature of at least 1800° C. In more preferred embodiments, the improved thermal stability is evidenced after heat treating the mesoporous carbon material at a temperature of at least 1850° C., 1900° C., 1950° C., 2000° C., 2050° C., 2100° C., 2150° C., 2200° C., 2250° C., 2300° C., 2350° C., 2400° C., 2450° C., 2500° C., 2550° C., 2600° C., 2650° C., or 2700° C. A "substantial absence of structural shrinkage" and a "substantial preservation of BET surface area", as used herein, generally means that either of these parameters change by no more than about 5%, and more preferably, no more than about 1%, 0.5%, or 0.1% after heat treatment as compared to the original value before heat treatment. A "substantial preservation of mesoporosity", as used herein, generally means that the pore volume due to micropores or macropores does not increase by more than about 5%, and more preferably, no more than about 1%, 0.5%, or 0.1%, as compared to the total pore volume.

In the method for regulating ion transport, the above-described mesoporous carbon membrane (i.e., "membrane") is positioned in a liquid such that one side of the membrane is in contact with a first region of the liquid and the other (opposing) side of the membrane is in contact with a second region of the liquid. For purposes of the invention, liquid flow between the first and second regions of the liquid is permitted only through the membrane. Thus, appropriate measures should be taken to ensure that liquid flows between first and second regions only through the membrane. Generally, one of the first or second region of liquid contains ionic species while the other of the first or second region of liquid is substantially removed of ionic species. In this way, liquid diminished in ionic species can be attained, i.e., by permitting liquid flow, absent the ionic species, from the ion-containing region to the region not containing ions. The liquid considered herein is typically water or an aqueous-based solution containing water and one or more co-solvents (e.g., an alcohol, ketone, or water-soluble ether) dissolved in the water.

A sufficient electric potential (voltage) is applied onto the mesoporous carbon membrane to modulate the degree of ion transport between the first and second regions of liquid. Generally, the voltage is up to or less than 1 volt, 0.5 volt, or 0.25 volt, or a voltage within a range between these values. The polarity of the voltage applied on the membrane is generally inconsequential. An increase in the applied voltage results in a reduction in the degree of ion transport between the first and second regions of the liquid. At a high enough voltage (i.e., "critical voltage"), ion transport ceases. For purposes of water purification, such as desalination, the membrane is generally operated at the critical voltage in order to maximize the purification process. The electrical power can be provided by any suitable source, including by standard electric power generation or batteries. In some embodiments, particularly in view of the lower electrical requirements of the above-described process, the electrical power may be provided by solar energy, i.e., by electrical communication (wiring means) between the membrane and one or more photovoltaic devices, such as photovoltaic (solar) panels.

In one embodiment, the method is a water purification method. In a first instance, the water purification method is a desalination method. In the case of desalination, the ionic species to be blocked by the membrane can be any dissolved inorganic salt, particularly those inorganic salts commonly found in seawater, such as sodium salts (NaY), potassium salts (KY), magnesium salts ($MgY_2$), and calcium salts ($CaY_2$), wherein Y represents an anion, include those selected from the halides (e.g., Cl— or Br—), sulfate, carbonate, and carboxylates. In a second instance, the water purification method is a waste removal or decontamination method, wherein the waste or contaminant (or a component of the waste or contaminants) is an organic or inorganic ionic species. The waste or contaminant can be any ionic species desired to be removed from water, and may be, for example, effluent from an industrial process or sewage treatment plant. Some examples of waste or contaminant species include, for example, ionic detergents and cleaners, metal ions, pharmaceutical salts, and ionic dyes. In either case, water purification generally employs a critical voltage at which ion transport ceases, in order to prevent ion transport from a first region into a second region while permitting flow of the liquid without ions through the mesoporous carbon membrane from the first region into the second region.

In another embodiment, the method is a chemical separation method in which at least one of the first and second regions of the liquid contains a dissolved organic ionic species. As in the case of water purification, discussed above, the chemical separation method generally employs a critical voltage at which ion transport ceases, in order to prevent ion transport from a first region into a second region while permitting flow of the liquid without ions through the mesoporous carbon membrane from the first region into the second region. In a particular embodiment, the chemical separation method is directed to a chemical reaction in which a reaction product becomes at least partially or substantially or completely separated from one or more reaction byproducts. In a first instance, the reaction product is ionic while one or more byproducts are non-ionic, in which case a critical voltage can be applied to the membrane in order to retain the ionic reaction product in a first region holding both the ionic reaction product and one or more byproducts. With the critical voltage applied on the membrane, the non-ionic reaction byproduct is permitted to flow through the membrane to a second region not containing the ionic reaction product. In a second instance, the reaction byproduct is ionic while the reaction product is non-ionic, in which case a critical voltage can be applied to the membrane in order to retain the ionic reaction byproduct in a first region holding both the reaction product and the ionic byproduct. With the critical voltage applied on the membrane, the non-ionic reaction product is permitted to flow through the membrane to a second region not containing the ionic reaction byproduct. A particular example of such a reaction is the reaction of an amine-containing compound (e.g., a pharmaceutical or dye) with an acid to form an ammonium salt of the amine-containing compound. In this case, the ammonium product can be retained at the critical voltage in a first region of the liquid while the neutral amine-containing starting compound can flow through the membrane into a second region of the liquid not containing the ammonium product. An analogous process can be used in a reaction in which a carboxylic acid-containing compound is reacted with a base to form a carboxylate salt product.

In yet another embodiment, the method is a method for the controlled intravenous release of an ionic drug to a patient. In some embodiments, the active pharmaceutical drug is, itself, ionic, whereas in other embodiments, the active pharmaceutical drug is non-ionic but is housed in or tethered to an ionic moiety in order to render the drug useful in the instant method of controlled intravenous release. In the method, the mesoporous carbon membrane separates a first region containing an ionic drug dissolved in an aqueous-based pharmaceutically acceptable medium and a second region containing an aqueous-based pharmaceutically acceptable medium flowing intravenously to the patient. The second region of liquid, which flows intravenously to the patient, does not contain the ionic drug when a critical voltage is applied to the membrane. At a voltage below the critical voltage, the ionic drug is permitted to flow from the first region into the second region flowing intravenously into the patient, wherein a lower voltage permits a higher rate of drug flow from the first region into the second region flowing intravenously into the patient. In this way, the rate of drug flow to the patient can be precisely regulated by appropriate selection of the voltage applied to the membrane. The ionic drug can be any drug to be administered intravenously, and may be, for example, an inorganic salt (e.g., magnesium sulfate or electrolyte) or an organic salt form of a pharmaceutical agent (e.g., the methanesulfonate form of vestipitant, an antidepressant and anti-emetic). The foregoing method for controlled intravenous release is particularly advantageous in that a concentrated solution of the drug (well beyond the acceptable limit for administration) may be housed in the first region containing the ionic drug in order to extend the term of use to the patient along with a significantly reduced requirement for replenishing the drug source.

Any of the exemplary methods, described above, in which regulation of ion transport is achieved, may further include a step of monitoring the ion concentration in the first and/or second regions separated by the mesoporous carbon membrane in order to correlate the degree of ion transport (ion flow) with the voltage used. The ion concentration or degree of ion flow can be monitored by, for example, monitoring electrical conductivity or ultraviolet-visible (UV-Vis) spectroscopic characteristics of the first and/or second regions. In this way, appropriate adjustments can be made to the voltage to attain a desired level of ion transport.

Examples have been set forth below for the purpose of illustration and to describe certain specific embodiments of the invention. However, the scope of this invention is not to be in any way limited by the examples set forth herein.

EXAMPLES

Preparation of Mesoporous Carbon Membrane

Free-standing mesoporous carbon-carbon black (MC-CB) nanocomposite membranes were synthesized by carbonization of polymeric composite films (125 μm in thickness) fabricated by casting an ethanolic solution of phenolic resin-CB-block copolymer (F127) composite on a hydrophilic Mylar™ sheet via a tape casting technique. The gel-like composite was obtained by self-assembly of in situ formed phloroglucinol-formaldehyde resin, CB, and F127 under acidic conditions. After removal of the air bubbles by centrifugation, the solution was casted into a thin film on a hydrophilic Mylar™ sheet via a doctor blade tape casting technique leading to a free-standing polymeric film (~100 μm in thickness) after drying overnight at room temperature and subsequent curing at 80° C. for 24 hours. The polymeric film was punched into small circular films with a diameter of 20 mm, detached from the substrate, carbonized after loading between two pieces of carbon paper, and sandwiched by quartz strips to maintain the flat-sheet morphology. The carbonization was conducted in flowing argon (100 mL/min) at 450° C. for 2 hours and subsequently at 850° C. for an additional 2 hours using a heating rate of 2° C./min.

Surface Etching and Characterization

Initially, the surface of the as-prepared membrane was found to be non-porous or microporous. Therefore, the thin surface layer was etched by exposing each side of the carbon membrane to an oxygen plasma for about 45 minutes. In order to characterize the pore volume and pore size, nitrogen-sorption analysis was conducted at −196° C. (77 K). Before measurement, the etched membrane was degassed in vacuum at 120° C. overnight. The specific surface area was estimated from the nitrogen adsorption data in the relative pressure range ($P/P_O$=0.06–0.03) using the Brunauer-Emmett-Teller (BET) method. The total pore volume was determined from the nitrogen uptake at $P/P_O$=0.95. The micropore volume was calculated from the intercept of the V-t plot ($V_m$=0.0015468*intercept), where the t values were calculated as a function of the relative pressure using the de Bore equation, $t/\text{Å}=[13.99/(\log(P/P_O)+0.0340)]^{1/2}$. The pore size distribution (PSD) plot was derived from the adsorption branch of the isotherm based on the BJH model. For surface images, a scanning electron microscope or a scanning transmission electron microscope was used.

Ion Permeation Measurements

The ion permeation experiments were conducted using a U-shaped cell. The U-shaped cell consisted of the source and the receiver solutions, separated by a mesoporous carbon membrane. The mesoporous carbon membrane was mounted between two pieces of adhesive-backed aluminum foil with a hole of 0.5 cm diameter in the center exposing the membrane. One side of the Al foil/membrane was further covered with plastic with a hole in between exposing the membrane to prevent any possibility of electrochemical reactions occurring on the source side of the U-shaped tube. Alligator clips were used to establish electrical connection, and the electrochemical potential ($E_{APP}$) was applied to the membrane using a potentiostat. A silver/silver chloride (Ag/AgCl) reference electrode and platinum counter electrode were used for all the measurements. The aqueous solutions of methylene blue (abbreviated as $MB^+$; $Cl^-$ salt) and methyl orange (abbreviated as $MO^-$; $Na^+$ salt) and KCl were used to test the ion transport measurements. The UV-Vis absorption experiments were conducted with a spectrophotometer. The absorption spectra were measured within a certain time interval, using 3 mL of the solution taken from the receiver compartment (~5 mL) of a cell. After measurement, the solution was brought back to the receiver compartment.

Results and Discussion

Figure 2A:
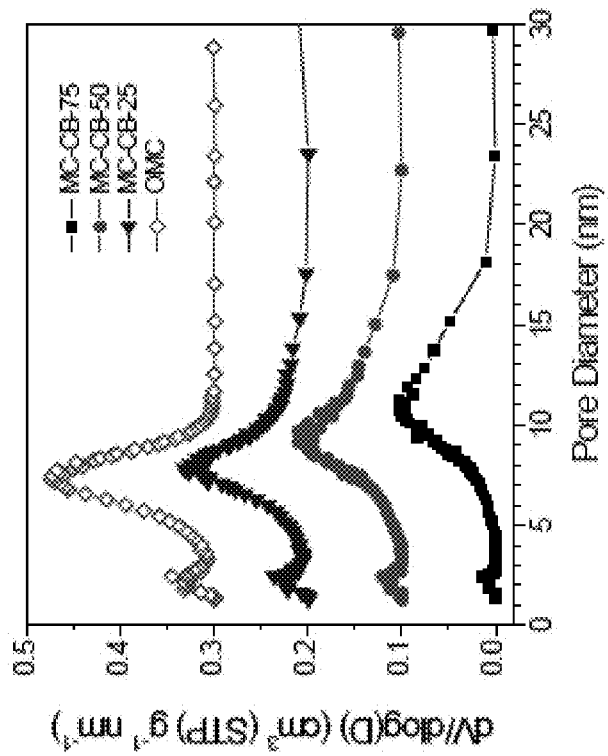
FIGS. 2A, 2B.
Figure 2B:
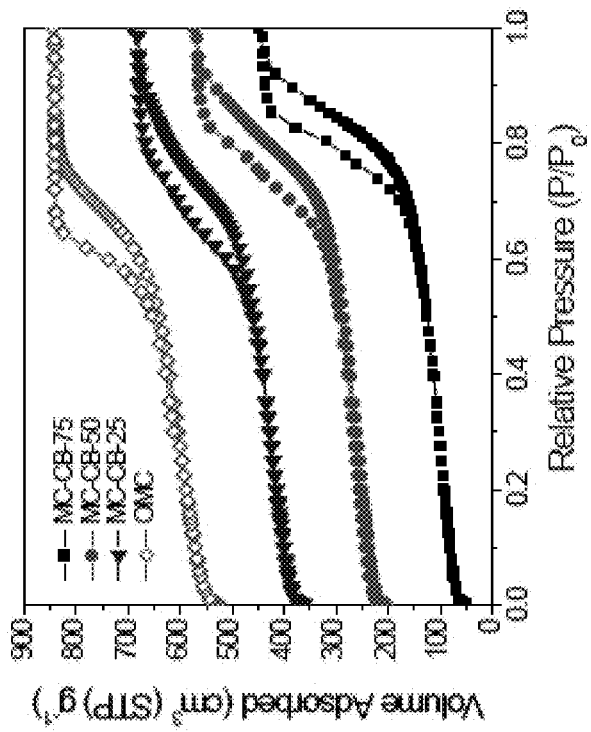

FIG. 1A is a representation of the mesoporous carbon membrane used to control the transport of ions. As illustrated in the figure, in the presence of an applied potential, ion transport through the membrane is inhibited. The mesoporous carbon-carbon black (MC-CB) nanocomposite membranes were created by incorporating carbon black into a typical soft-templating synthesis method, as described, for example, in Fulvio, P. F., et al., "Brick-and-mortar" self-assembly approach to graphitic mesoporous carbon nanocomposites, *Adv. Funct. Mater.*, 21, pp. 2208-2215, 2011, the contents of which are herein incorporated by reference. Membranes with carbon black initially varying from 25%-75% were synthesized to primarily control the pore size and electrical conductivity of the material. An added advantage of incorporating CB into the composite was the improved stability of the membrane since the MC-CB composite membrane was less fragile and more mechanically robust than the pristine mesoporous carbon membrane. FIG. 1B shows the SEM image of the carbon membrane. The SEM image indicates small pores on the surface. FIG. 2A shows the nitrogen-physisorption isotherms and pore size distributions of the MC-CB nanocomposite membranes. The adsorption isotherms (type IV) and hysteresis loops (H-1) for all MC-CB nanocomposite membranes are typical for materials with large mesopores (FIG. 2A). As the CB content increased from 0 to 75 wt. %, the pore size distribution (FIG. 2B) changed from a relatively narrow distribution centered at 7.3 nm to a broader distribution centered at 11.3 nm, while with the BET surface area decreased from 493 to 324 $m^2\ g^{-1}$ (Table 1, below). Thus, the pore size of the carbon could be controlled by controlling the amount of carbon black.

TABLE 1

Textural properties of MC-CB composite membranes.

| Sample | MC-CB-0 | MC-CB-25 | MC-CB-50 | MC-CB-75 |
|---|---|---|---|---|
| $S_{BET}$ ($m^2\ g^{-1}$)[a] | 493 | 406 | 352 | 324 |
| $S_{mi}$ ($m^2\ g^{-1}$)[b] | 369 | 311 | 270 | 245 |
| $V_{SP}$ ($cm^3\ g^{-1}$)[c] | 0.61 | 0.58 | 0.65 | 0.68 |
| $V_{mi}$ ($cm^3\ g^{-1}$)[d] | 0.06 | 0.04 | 0.04 | 0.04 |
| w (nm)[e] | 7.3 | 7.8 | 9.7 | 11.3 |

[a]specific surface area calculated using the BET equation in the relative pressure range of 0.05-0.20;
[b]micropore surface area calculated in the αS-plot range of 0.80-1.00;
[c]single point pore volume from adsorption isotherms at p/p0 ~0.98;
[d]micropore volume calculated in the αS-plot range of 0.80-1.00;
[e]pore width calculated according to the improved KJS method using statistical film thickness for nonporous reference carbon material.

Figures 3A, 3B:
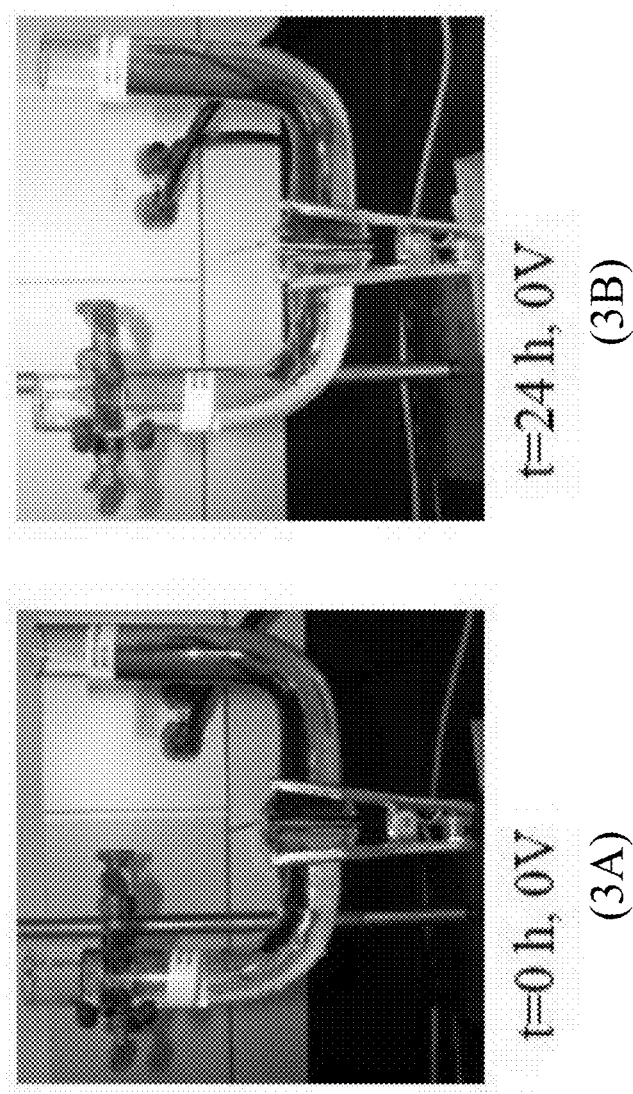
FIGS. 3A, 3B. Photos of the experimental set-up in which the mesoporous carbon membrane is partitioned in the middle of a U-shaped tube separating a first region (right side of tube containing source of ionic dye) and second region (left side of tube containing only D.I. water), at 0 hours (FIG. 3A) and 24 hours (FIG. 3B) with no applied voltage (0 V). Two ionic dyes were used: methyl orange ($MO^-$), which is an anionic dye, and methylene blue ($MB^+$), which is a cationic dye. For each dye, the D.I. water in the receiver side of the U-shaped tube turned orange or blue after 24 hours, which indicates diffusion of dye molecules through the membrane.

Because the MC-CB composite membrane with 25% carbon black (i.e., "MC-CB-25") had the smallest pore size of all the composites, hence the highest potential for electrochemical control, the experiments focused on the MC-CB-25 membrane. The ion permeability through the MC-CB-25 membrane was first tested without an electrochemical potential. Ion transport for two different dye solutions, e.g. methyl orange as the cationic ion and methylene blue as an anionic ion, were initially examined as a visual demonstration of the transport properties as a function of applied potential. Two source solutions were prepared: (1) the cationic source solution was 0.5 mM methylene blue ($MB^+$) and 1 mM KCl and (2) the anionic source solution was 0.5 mM methyl orange ($MO^-$) and 1 mM KCl in deionized (D.I.) water. As shown in FIG. 3A, the source solution was placed on the right side of the U-shaped tube while the receiver (left) side contained D.I. water. Each solution was used separately to avoid possible precipitation between MB$^+$ and MO$^-$. After a retention time of approximately 4 hours, both MB$^+$ and MO$^-$ species were detected at the receiver side of the U-shaped cell by UV-Vis absorption spectroscopy. Significantly, the concentrations of both species gradually increased with increasing retention time, as evidenced in FIG. 3B, which shows the U-shaped tube after 24 hours.

Figure 4:
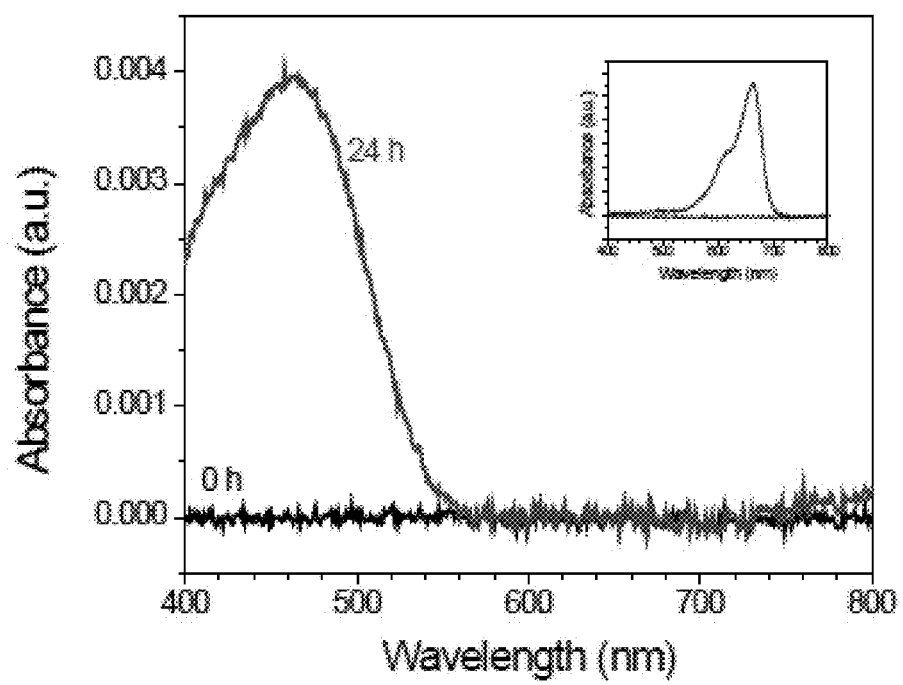
FIG. 4. UV-Visible absorbance spectra of methyl orange at 0 hours and after 24 hours with no applied potential. The inset shows similar UV-Vis spectra for methylene blue. As shown, the spectra confirm significant diffusion of dye molecules across the membrane after 24 hours.

FIG. 4 shows the UV-Vis absorption spectra of MB$^+$ and MO$^-$ measured at the receiver side after a retention time of 8 hours. Both cations (MB$^-$) and anions (MO$^-$) were transported by diffusion driven by a concentration gradient across the membrane. These results were quite reproducible and similar to previous results obtained with anilinium and Rhodamine B (Hou, C.-H., et al., "Molecular-sieving capabilities of mesoporous carbon membranes", *J. Phys. Chem. B*, 112, pp. 8563-8570, 2008). In the absence of an applied potential, both cations and anions diffused through the membrane with no gating or separation selectivity.

Figures 5A, 5B:
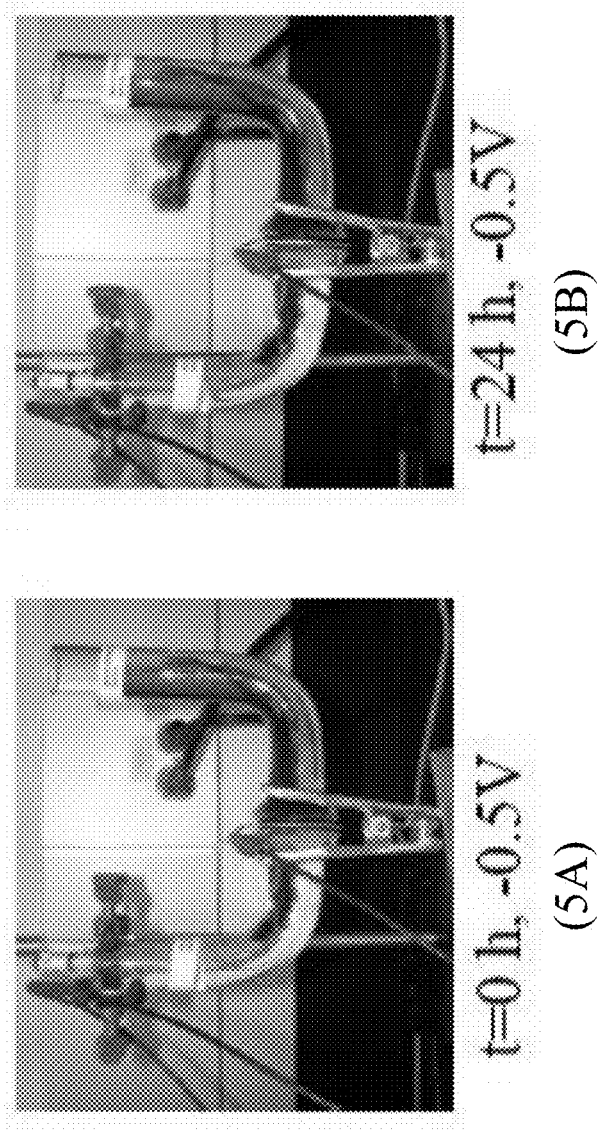
FIGS. 5A, 5B. Photos of the experimental set-up, same as in FIGS. 3A, 3B, in which the mesoporous carbon membrane is partitioned in the middle of a U-shaped tube separating a first region (right side of tube containing source of ionic dye) and second region (left side of tube containing only D.I. water), at 0 hours (FIG. 5A) and 24 hours (FIG. 5B) at an applied voltage of −0.5 V. No change in the color of the D.I. water in the receiver side of the U-shape tube was observed after 24 hours, which indicates no dye diffusion through the membrane.
Figure 6:
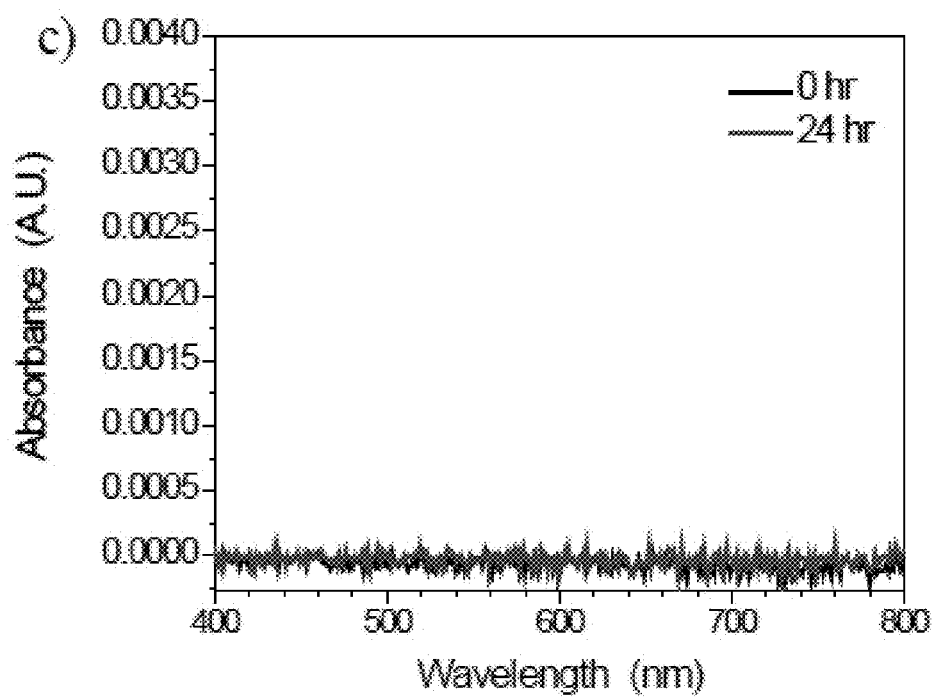
FIG. 6. UV-Visible absorbance spectra of methyl orange at 0 hours and after 24 hours at an applied voltage of −0.5 V. As shown, the spectra confirm no diffusion of dye molecules across the membrane after 24 hours.

In contrast, the results were remarkably different with the application of an electrical potential to the membrane. With application of an electrical potential, no ion transport was observed through the membrane. More specifically, when an electrochemical potential of −0.5 V was applied to the membrane in the same U-shaped tube, as shown in FIGS. 5A and 5B (0 hours and 24 hours, respectively), no spectral evidence of the anionic dye MO$^-$ was observed in the receiver solution even after 24 hours, as further confirmed by the UV-Vis absorbance spectra shown in FIG. 6. Similar results were obtained for the cationic dye MB$^+$. Unlike ion-selective membranes, the polarity of the potential did not matter and the diffusion of dye ions through the membrane was prohibited when a potential was applied regardless of polarity.

A possible mechanism for this gating effect observed in the dye solutions is that the electrical double layer (EDL) in the pores of the carbon membrane was larger than the pore radius, which results in an overlapped EDL within the pores. The pore diameter for the MC-CB-25 membrane is ~7.8 nm, while the Debye length of the ion solution was estimated to be ~9 nm using the following equation:

$$\lambda_D = \sqrt{\frac{\varepsilon_0 \varepsilon_r RT}{2F^2 C_0}}$$

In the above equation, $\varepsilon_0$ is permittivity of free space, $\varepsilon_r$ is the dielectric constant of the solution, R is the gas constant, T is the temperature, F is the Faraday constant, and $C_0$ is the electrolyte concentration. Thus, the electrostatic field readily extended throughout the channel, which enabled control over the transport of ions using the electrochemical potential. When the voltage was in the range of 0 to −0.4 V, the electrostatic field was not strong enough to shield the entire cross-section of the channel, which allowed the dye molecules to diffuse through the membrane and be detected at the receiver end. However, the stronger electric field at −0.5 V prevented the passage of dye ions through the membrane, regardless of the charge of the ion.

To further confirm that this was indeed an EDL effect, the Debye length of the solution was decreased by increasing the salt concentration from 1 mM KCl to 0.25M KCl and repeating the dye transport measurements using a 0.5 mM dye solution. The Debye length of the 0.25 M KCl solution was ~0.6 nm, which is much smaller than the pore radius of the carbon membrane. Even with an electric potential applied to the membrane, transport of the dye through the membrane was observed on the receiver side, which confirms that this is indeed an EDL effect.

Figure 7A:
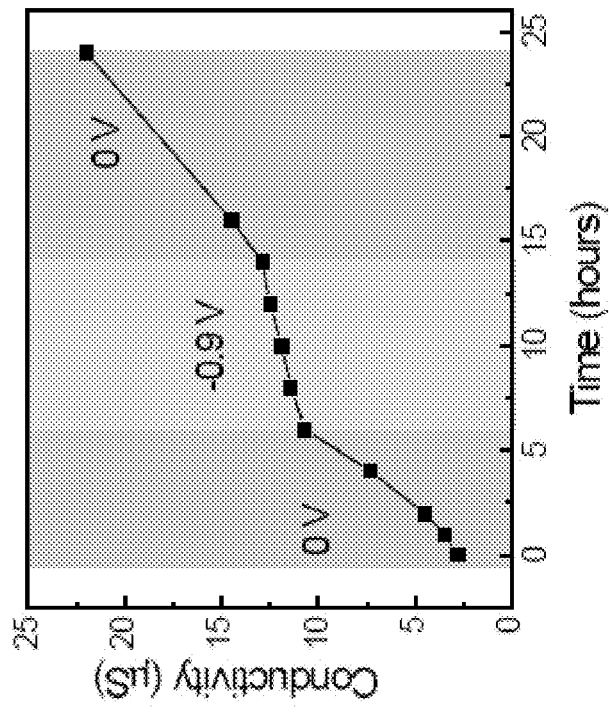
FIGS. 7A, 7B.

Based on the ability to gate the large dye ions and to evaluate the potential of the carbon membranes to control the transport of smaller salt ions for application in desalination, the measurements were repeated using KCl rather than the molecular (dye) ions. Briefly, 1 mM KCl was used as the source solution, and the receiver side of the U-shaped glass tube was filled with D.I. water. The conductivity of the D.I. water in the receiver side was continuously monitored over time. As shown in the conductivity vs. time plot in FIG. 7A, in the absence of an electrical potential on the membrane, the conductivity of the receiver solution continuously increased, which indicates ion diffusion through the membrane. However, when an electrical potential of −0.9 V was applied to the membrane, ion transport through the membrane was drastically reduced. There was no significant effect on the diffusion rate when the applied potential was less than −0.8 V. However, when the potential was increased to −0.9 V, ion transport through the membrane was inhibited.

Figure 7B:
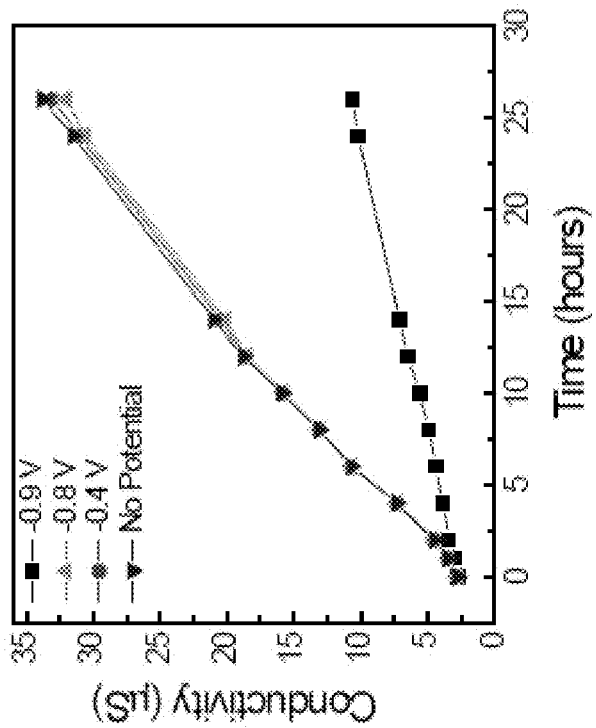

Because the K$^+$ and Cl$^-$ ions are much smaller than the organic dye molecules, a larger applied potential was necessary to prevent ion transport through the membrane. To further confirm that this effect was not due to an electrochemical reaction at the electrode surface causing pore blockage, the potential at the membrane was sequentially applied and then removed. As shown in the conductivity vs. time plot in FIG. 7B, when no potential was applied to the membrane, the ions freely flowed through the membrane; however, when a potential was applied, the rate at which ions passed through the membrane decreased, as indicated by the change in the slope. When the potential was removed, the rate at which ions flowed through the membrane increased. Interestingly, the rate of ion flow at 0 V after applying −0.9 V was slightly lower than the initial flow rate at 0 V.

In summary, the above results demonstrate the utility of a mesoporous carbon-based bulk nanofluidic transport membrane for regulation of ion transport. As demonstrated, the method can be effectively applied to a wide range of ionic species, including large organic molecules (e.g., dyes) and smaller ions (e.g., metal and halide ions). Moreover, the method achieves this using a low electrochemical potential less than 1 V. As the transport of ions was found to not depend on the polarity of the potential applied to the membrane, the membrane can directly function as an on/off (gated) switch, which allows for gated control of a wide range of ionic species. This unique property of the mesoporous carbon membranes described herein opens up further and greater opportunities in a number of applications, including controlled drug release, desalination, and chemical separations.

While there have been shown and described what are at present considered the preferred embodiments of the invention, those skilled in the art may make various changes and modifications which remain within the scope of the invention defined by the appended claims.

What is claimed is:

1. A method for regulating ion transport between first and second regions of a liquid solution containing ionic species in at least one of said first and second regions, the method comprising applying a voltage on a single electrically conductive mesoporous carbon membrane situated between said first and second regions of the liquid solution, wherein liquid flow between first and second regions is permitted only through said mesoporous carbon membrane, and the applied voltage is selected to modulate the degree of ion transport between said first and second regions, wherein an increase in applied voltage results in a reduction in the degree of ion transport between said first and second regions, optionally up to a critical voltage at which ion transport ceases, wherein said single electrically conductive mesoporous carbon membrane functions by hindering or blocking the transport of ions instead of absorbing the ions when applying said applied voltage, wherein the method does not include a step of desorbing the ions from the single electrically conductive mesoporous carbon membrane, and wherein said single electrically conductive mesoporous carbon membrane also includes: (i) a pore size distribution centered at 7.3 nm and having a degree of variation in pore size of ±3 nm from 7.3 nm, and (ii) conductive carbon nanoparticles embedded therein in an amount of 1-25 wt %.

2. The method of claim 1, wherein said liquid solution is aqueous-based.

3. The method of claim 1, wherein said mesoporous carbon membrane contains mesopores having a pore size of 2 to 30 nm.

4. The method of claim 1, wherein said mesoporous carbon membrane contains mesopores having a pore size of 2 to 20 nm.

5. The method of claim 1, wherein said macropores are substantially absent in the mesoporous carbon membrane.

6. The method of claim 1, wherein said applied voltage is up to one volt.

7. The method of claim 1, wherein said applied voltage is provided by solar energy.

8. The method of claim 7, wherein said solar energy is provided by at least one photovoltaic device in electrical communication with said conductive mesoporous carbon membrane.

9. The method of claim 1, wherein said method is a desalination method in which the liquid in said first region contains a dissolved inorganic salt, and said critical voltage at which ion transport ceases is applied on said mesoporous carbon membrane to prevent ion transport from said first region into said second region while permitting flow of the liquid without ions through the mesoporous carbon membrane from said first region into said second region.

10. The method of claim 9, wherein the liquid in said first region is seawater.

11. The method of claim 9, wherein said critical voltage is provided by solar energy.

12. The method of claim 11, wherein said solar energy is provided by at least one photovoltaic device in electrical communication with said conductive mesoporous carbon membrane.

13. The method of claim 1, wherein said method is a chemical separation method in which the liquid in at least one of said first and second regions contains a dissolved organic ionic species, and said critical voltage at which ion transport ceases is applied on said mesoporous carbon membrane to prevent ion transport of organic ionic species between said first and second regions while permitting flow of the liquid without said organic ionic species through the mesoporous carbon membrane.

14. The method of claim 13, wherein said organic ionic species is a reaction byproduct, whose separation from a non-ionic reaction product results in a purified reaction product.

15. The method of claim 13, wherein said organic ionic species is a reaction product, whose separation from a non-ionic reaction byproduct results in a purified reaction product.

16. The method of claim 1, wherein said method is a method for controlled intravenous release of an ionic drug to a patient, wherein said first region comprises said ionic drug dissolved in an aqueous-based pharmaceutically acceptable medium, and said second region flows intravenously to a patient and contains said aqueous-based pharmaceutically acceptable medium without said ionic drug except as permitted by passage of the ionic drug through the mesoporous carbon membrane, and wherein a rate of drug flow from said first region to said second region, and hence, rate of drug flow to the patient, is determined by appropriate selection of the voltage applied to the mesoporous carbon membrane that separates said first and second regions.

17. The method of claim 1, further comprising, during or after said regulation of ion transport, a step of monitoring the ion concentration in said first or second region in order to correlate the degree of ion transport with the voltage used.

18. The method of claim 17, wherein the ion concentration is monitored by monitoring electrical conductivity or ultraviolet-visible spectroscopy of said first or second region.

19. The method of claim 1, wherein said pore volume attributed to said micropores is at least 50%.

20. The method of claim 1, wherein said single electrically conductive mesoporous carbon membrane also includes: (iii) micropores having a pore size of less than 2 nm in a pore volume attributed to said micropores of over 45%, and (iv) a pore volume attributed to macropores of 0-1%, wherein said macropores have a pore size greater than 50 nm.

* * * * *